United States Patent
Manai et al.

(10) Patent No.: US 9,226,806 B2
(45) Date of Patent: Jan. 5, 2016

(54) OCCLUSION ESTIMATION IN DENTAL PROSTHESIS DESIGN

(75) Inventors: Myriam Manai, Quebec (CA); David Giasson, Quebec (CA); Bin Hang, (Saint-Nicolas), Lévis (CA)

(73) Assignee: Biocad Medical, Inc., Quebec (CA)

( * ) Notice: Subject to any disclaimer, the term of this patent is extended or adjusted under 35 U.S.C. 154(b) by 472 days.

(21) Appl. No.: 12/884,669

(22) Filed: Sep. 17, 2010

(65) Prior Publication Data
US 2012/0072177 A1    Mar. 22, 2012

(51) Int. Cl.
| G06G 7/48 | (2006.01) |
| G06G 7/60 | (2006.01) |
| A61C 11/00 | (2006.01) |
| A61C 13/00 | (2006.01) |
| A61C 13/097 | (2006.01) |

(52) U.S. Cl.
CPC .............. *A61C 11/00* (2013.01); *A61C 13/0004* (2013.01); *A61C 13/097* (2013.01)

(58) Field of Classification Search
None
See application file for complete search history.

(56) References Cited

U.S. PATENT DOCUMENTS

| 5,458,487 | A | 10/1995 | Komatsu et al. |
| 5,531,520 | A | 7/1996 | Grimson et al. |
| 5,800,174 | A | 9/1998 | Andersson |
| 6,152,731 | A | 11/2000 | Jordan et al. |
| 6,319,006 | B1 | 11/2001 | Scherer et al. |
| 6,334,853 | B1 | 1/2002 | Kopelman et al. |
| 6,979,196 | B2 | 12/2005 | Nikolskiy et al. |
| 8,199,988 | B2 | 6/2012 | Marshall et al. |
| 8,234,000 | B2 | 7/2012 | Andersson et al. |
| 8,425,229 | B2 | 4/2013 | Nilsson et al. |
| 2004/0029068 | A1* | 2/2004 | Sachdeva et al. ............... 433/24 |
| 2004/0172150 | A1 | 9/2004 | Perot et al. |
| 2006/0063135 | A1 | 3/2006 | Mehl |
| 2010/0106275 | A1 | 4/2010 | Andersson et al. |
| 2010/0151417 | A1 | 6/2010 | Nilsson et al. |
| 2010/0332248 | A1 | 12/2010 | Pettersson |

(Continued)

FOREIGN PATENT DOCUMENTS

| WO | WO 98/52493 | 11/1998 |
| WO | WO 03/092536 | 11/2003 |
| WO | WO 2004/044787 | 5/2004 |

OTHER PUBLICATIONS

Olthoff et al. "Computer modeling of occlusal surfaces of posterior teeth with the CICERO CAD/CAM System", Journal of Prosthetic Dentistry, 2000, vol. 84 No. 2, pp. 154-162.*

(Continued)

*Primary Examiner* — Suzanne Lo
(74) *Attorney, Agent, or Firm* — Knobbe Martens Olson & Bear, LLP

(57) ABSTRACT

Herein are provided methods, systems, computer-readable media, techniques and processes for occlusion estimation in dental prosthesis design. These include determining a first contact point between antagonist teeth, then simulating motion in order to determine additional contact points. Various of the determined contact points may not be used in the simulated motion, based on the simulated physics. When one or more predetermined stopping criteria have been met, then the contact points may be used to define the relative occlusal positions of antagonists. In some embodiments, sets of teeth in a bridge or crown, e.g., may be simulated as moving separately and a new state for each set of teeth may be determined.

27 Claims, 17 Drawing Sheets

(56) References Cited

U.S. PATENT DOCUMENTS

| | | |
|---|---|---|
| 2011/0008751 A1 | 1/2011 | Pettersson |
| 2011/0010187 A1 | 1/2011 | Andersson et al. |
| 2011/0060558 A1 | 3/2011 | Pettersson et al. |
| 2011/0183291 A1 | 7/2011 | Carvalho et al. |
| 2011/0189625 A1 | 8/2011 | Hultgren et al. |
| 2011/0196524 A1 | 8/2011 | Giasson et al. |
| 2012/0070803 A1 | 3/2012 | Manai et al. |
| 2012/0129126 A1 | 5/2012 | Nouriam et al. |
| 2012/0171642 A1 | 7/2012 | Mehl |
| 2012/0282567 A1 | 11/2012 | Nilsson |
| 2012/0284000 A1 | 11/2012 | Nilsson |
| 2012/0290116 A1 | 11/2012 | Andersson et al. |

OTHER PUBLICATIONS

Hannam et al. "A dynamic model of jaw and hyoid biomechanics during chewing" 2008, Journal of Biomechanics 41, pp. 1069-1076.*
International Search Report issued in PCT Application No. PCT/IB2011/003064, dated Apr. 30, 2012, in 5 pages.
Written Opinion of the International Searching Authority issued in PCT Application No. PCT/IB2011/003064, dated Apr. 30, 2012, in 4 pages.

* cited by examiner

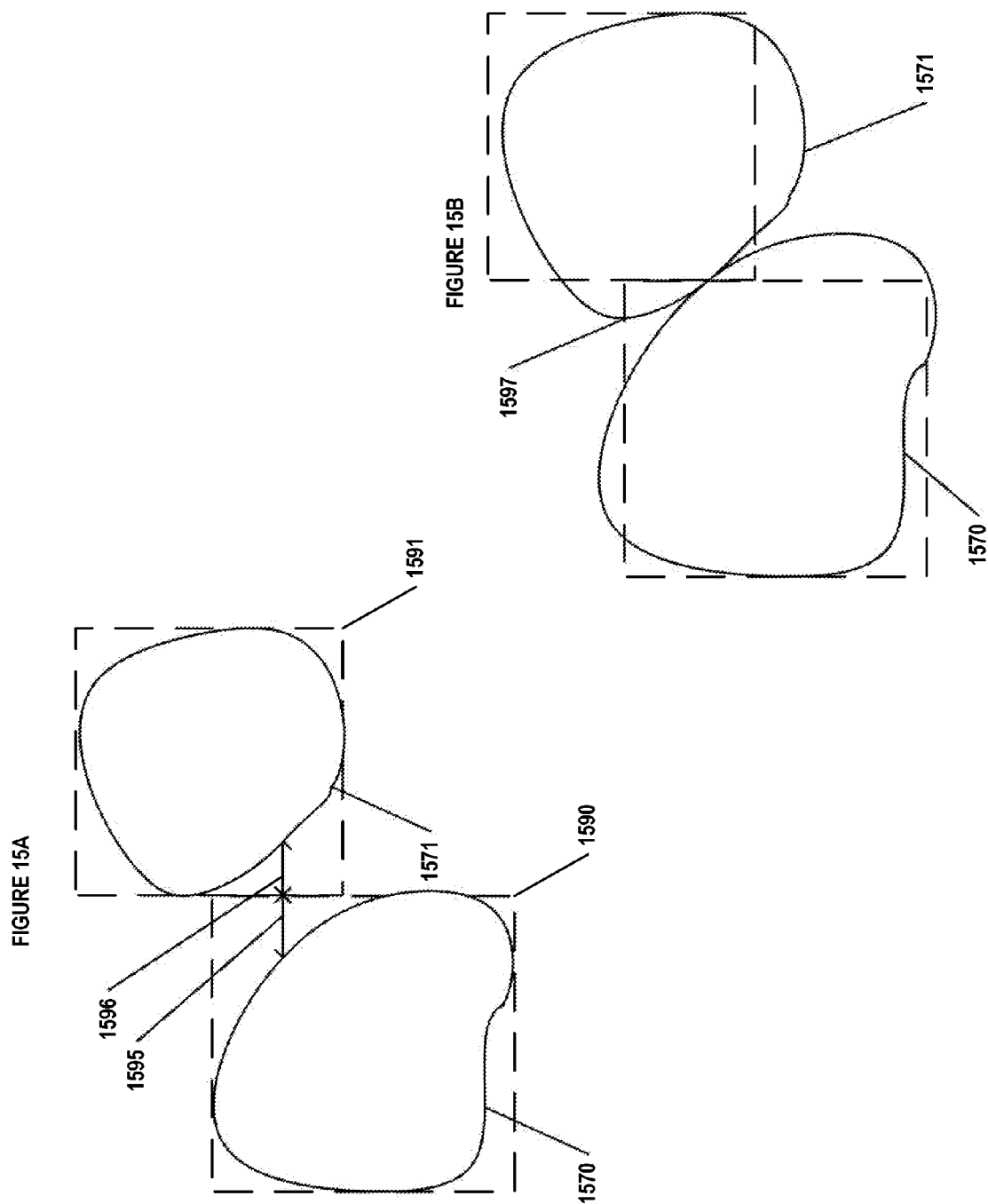

OCCLUSION ESTIMATION IN DENTAL PROSTHESIS DESIGN

BACKGROUND

1. Field

The present application generally relates to dental planning, and more particularly to occlusion estimation in dental prosthesis design.

2. Description of Related Technology

The use of computer systems to design dental prostheses has increased in recent years. The computer systems allow a dentist, dental technician, or other operator to design dental prostheses for individual patients. Individual prosthesis designs are often called "situations," "dental plans," or "prosthetic plans." Operators using the computer systems can design plans based on a library of the teeth shapes and positions, patient data, and available equipment and hardware.

When designing dental prostheses, a tooth or set of teeth's occlusion with antagonist teeth can be a factor in both function and aesthetics. Additionally, manipulating individual prosthetic teeth (or sets of individual prosthetic teeth) in a multi-tooth prosthesis can be difficult. When the upper set of teeth and the lower set of teeth have been scanned separately, it can be difficult to determine the occlusion between these occluding teeth. The difficulty may arise because the restrictions imposed by the temporomandibular joint (TMJ) of the jaw or other anatomy of the patient may be absent from the design software. Even when the TMJ and/or other restricting anatomy are represented in the design software, the operator may still need to estimate the occlusion between occluding teeth. Current techniques for providing occlusion estimation are not adequate and can be computationally expensive. The techniques, systems, methods, and computer-readable storage medium described herein overcome some issues associated with the prior art and provide for occlusion estimation and/or crown manipulation in dental prosthesis design.

SUMMARY

Presented herein are methods, systems, devices, and computer-readable media for occlusion estimation in dental prosthesis design. This summary in no way limits the invention herein, but instead is provided to summarize a few of the embodiments.

Embodiments herein include techniques, methods, systems, devices, and computer-readable media for occlusion estimation in dental prosthesis design. These can include determining, based on an initial relative placement of a first 3D model of teeth and a second 3D model of teeth, a first contact point on the first 3D model of teeth that is closest to the second 3D model of teeth, wherein the first 3D model of teeth and the second 3D model of teeth represent occluding teeth. Motion simulation of relative motion between the first 3D model of teeth and the second 3D model of teeth may be iteratively performed and may include determining, using a first set of contact points between the first 3D model of teeth and the second 3D model of teeth, a second set of contact points, said first set of contact points initially comprising the first contact point; determining a set of candidate contact points to use in a subsequent motion simulation iteration based on the second set of contact points; and determining whether the set of candidate contact points meets one or more predetermined stopping criteria. When a particular set of candidate contact points meets the one or more predetermined stopping criteria, a new relative placement of the first 3D model of teeth and the second 3D model of teeth may be determined based at least in part on the particular set of candidate contact points.

Some embodiments include receiving a 3D model of a multi-tooth prosthesis and a 3D model of antagonist teeth for the multi-tooth prosthesis, said multi-tooth prosthesis comprising 3D models of one or more prosthetic teeth. At least one contact point between the 3D model of antagonist teeth and each of the 3D models of one or more prosthetic teeth can be determined. A new shape for the 3D model of the multi-tooth prosthesis can be determined at least in part based on the determined contact points between the 3D model of the antagonist teeth and the 3D models of one or more prosthetic teeth.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIGS. 15A and 15B illustrate two schematics for prosthesis manipulation in dental prosthesis design.

DETAILED DESCRIPTION OF SPECIFIC EMBODIMENTS

Occlusion Estimation in Dental Prosthesis Design

Figure 1A:
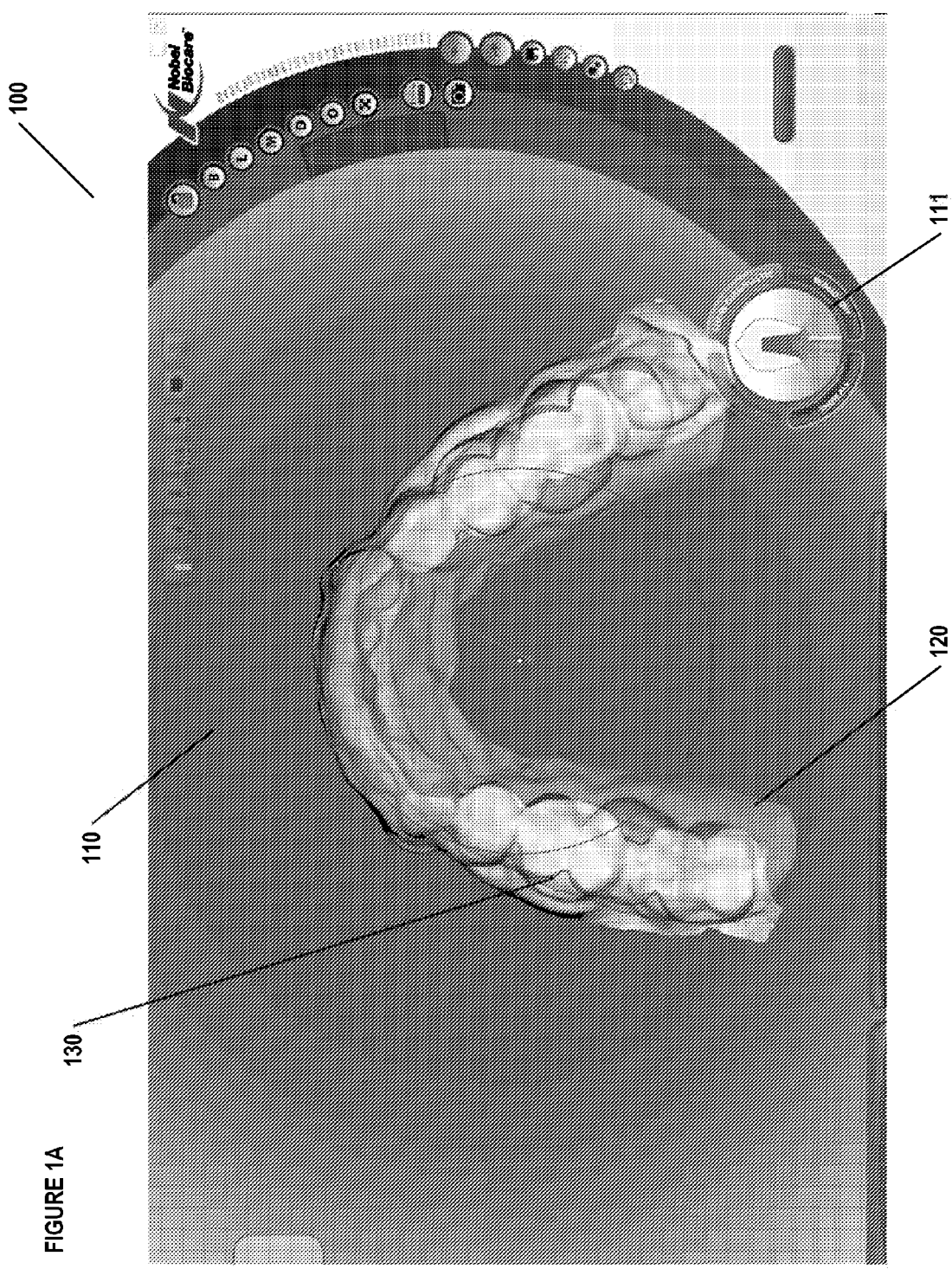
FIGS. 1A and 1B illustrate two interfaces for occlusion estimation in dental prosthesis design.

Various embodiments for occlusion estimation in dental prosthesis design are described herein. Some embodiments provide improved occlusion estimation over current systems. In some embodiments, initial placement of occluding teeth (before estimating occlusion) is either defined by the relative placement of the upper and lower teeth during intraoral scanning, during the scanning of the occluding teeth's physical models, by using a scanned checkbite, and/or by an operator manipulating one or both of the 3D models associated with the occluding teeth in order to obtain an initial relative placement. After an initial relative placement has been defined, the techniques may include finding a first contact point between the two 3D models (e.g., in the gravity direction). This can be done by determining using a distance calculation, for example, the closest points between the two 3D models. Another method for finding the first contact point between the two 3D models could be simulating one of the two 3D models 'falling' onto the other. After the first contact point has been determined (and if it has not already been accomplished), one of the 3D models can be translated in the gravity direction in order to bring the two 3D models together at that first contact point. The first contact point can be used as a pivot in a motion simulation, such as a six-degree of freedom motion simulation, a constrained rigid body motion simulation, a free-fall simulation, etc.

Once the pivot point is determined, the techniques may proceed by simulating the motion of one of the 3D models with respect to the other where the pivot point is used to restrict the rotation. For example, if the first contact point had been between the cusp of one tooth and the fissure of its antagonist tooth, then the two 3D models remain together at that point, and that point can act as a pivot, as one of the 3D models rotates with respect to the other around that point. The simulated rotation continues until one or more contact point(s) are detected. The contact points are detected at each step of the simulation by a collision detection engine. That is, once one of the 3D models has rotated onto the other 3D model and the corresponding contact points are determined with enough precision, that step of the simulation is terminated. If only one contact point is found, this contact point is used as a pivot in the subsequent step, regardless of whether or not it is the same contact point as in the previous step ('losing' a contact point could be caused, for example, by numerical error or imprecision). In various embodiments, an attempt to improve the precision of contact points determined may include, once one or more contact points are found, refining the previous simulation step with smaller and smaller step sizes (e.g., simulating motion simulation over smaller amounts of time) to reduce any interpenetration of the two 3D models.

If no contact point is found, that is if the contact point or contact points in the previous step are lost (for instance due to numerical imprecision), a motion simulation, such as a free fall, may be performed until a contact point is determined. In the case in which more than one contact point has been determined, then a check may be performed to determine what contact point(s) to use from the set of discovered contact points. Another motion simulation step may proceed using some or all of the candidate contact points (e.g., one or two of the candidate contact point may be used). A subsequent motion simulation step using two candidate contact points may include using the two candidate contact points to define an axis of rotation in the simulated motion. The process of determining new candidate contact points will continue until predetermined stopping criteria are met. Examples of stopping criteria are discussed more below.

In some embodiments, the 3D model of the teeth that is "moving" (e.g., the upper teeth) with respect to the other 3D model (e.g., the lower teeth) will have associated with it a center of gravity. The center of gravity can be determined in numerous ways. For example, the center of gravity may be determined by assigning a weight to each of the triangles, vertices, pixels, or voxels that form the 3D model and determine a center of gravity based on those assigned weights. In some embodiments, the predetermined stopping criteria may be met once there are three contact points that define a triangle that encompasses the center of gravity. Once this stopping criterion is met, the simulation may be terminated and the occlusion may be estimated based on those three contact points—those three contact points may define the placement of one of the 3D models with respect to another 3D model. For example, if the top set of teeth is seen as the moving set of teeth and a first contact point is determined between the top set of teeth and the lower set of teeth, then the first contact point may be used as a pivot point. The simulation may continue until subsequent contact points are determined that define a triangle that includes or encompasses the center of gravity of the top set of teeth.

In some embodiments, there may be a single stopping criterion that is met when there are two contact points on opposite sides of the center of gravity. For example, if a crown and its antagonist are the subjects of the occlusion estimation, then candidate contact points may be determined until there are two contact points that span or are on opposite sides of the center of gravity of the moving body. In some embodiments, the stopping criterion (a) may be met when the force normals acting on the moving body are such that no additional rotation is possible in the motion simulation.

Figure 1B:
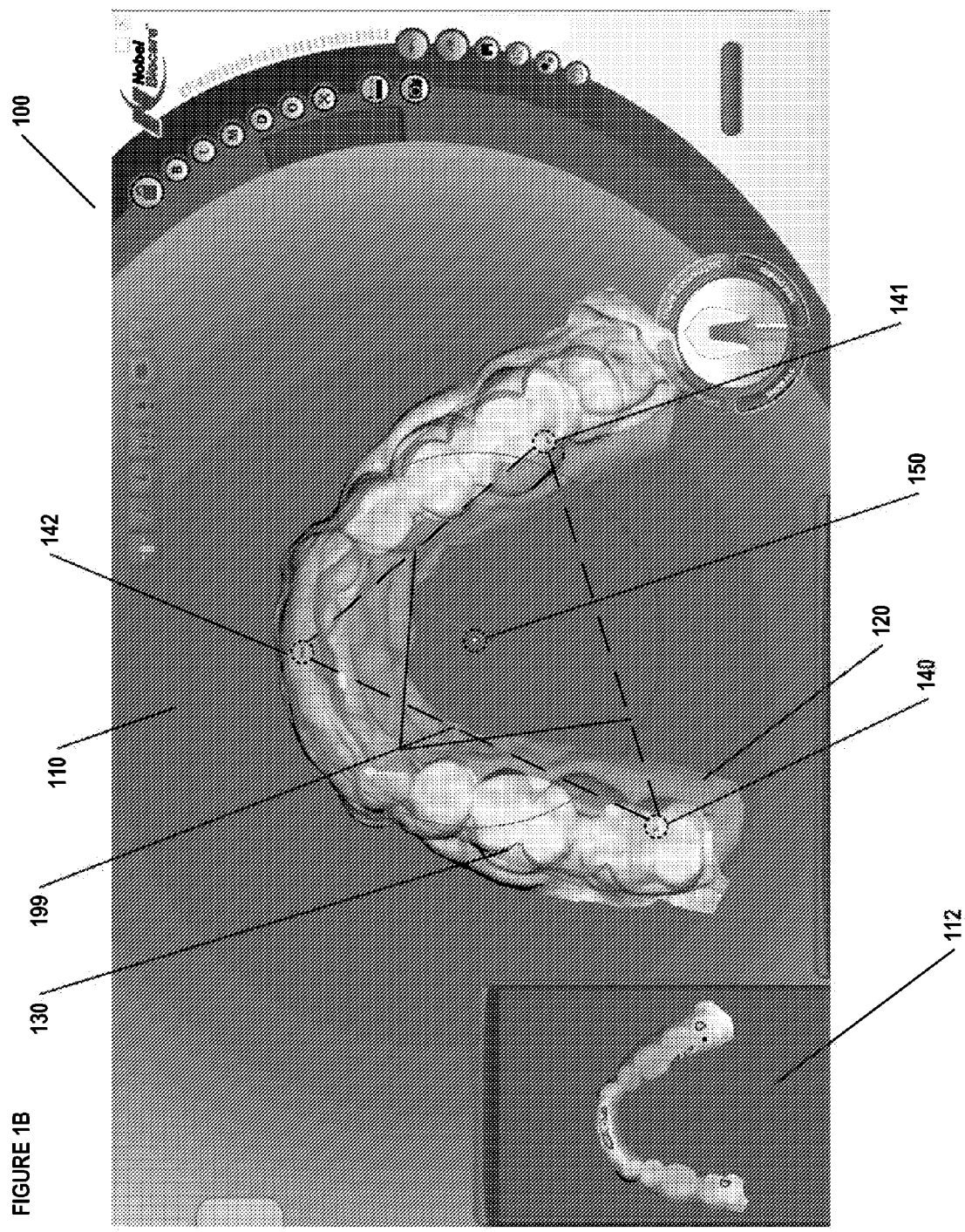

Turning now to FIG. 1A, we see an interface 100 that includes an overlaid representation portion 110 as well as a global selection portion 111. The overlaid representation portion 110 may display a lower teeth model 120 and an upper teeth model 130. The lower teeth model 120 may be represented as an opaque 3D model and the upper teeth model 130 may be represented as a transparent or semitransparent 3D model. The global selection portion may have buttons that allow either or both of the lower teeth model 120 and upper teeth model 130 to be displayed transparently or to provide other global manipulation functions. As depicted in FIG. 1B, an interface 100 may also include a distance map portion 112. The distance map portion 112 may show the distance between the lower teeth model 120 and the upper teeth model 130 as a contour graph, a color-coded graph, a shaded graph, and/or the like. This distance map may also be displayed, in some embodiments, as a texture map on the models 120 and/or 130 shown in the overlaid representation portion 110. Returning again to FIG. 1A, the interface 100 shows the lower teeth model 120 and the upper teeth model 130 before the occlusion estimation has occurred. FIG. 1B, on the other hand, shows the model 120 and the model 130 after the occlusion estimation has occurred. As depicted in FIG. 1B, after the first contact point has been determined between the lower teeth model 120 and the upper teeth model 130, that contact point can be used as a pivot to determine a subsequent set of one or more candidate contact points. The determination of candidate contact points may continue until three candidate contact points 141, 140, 142 are determined that define a triangle 199 that encompasses or includes the center of gravity 150.

Example System

Figure 2:
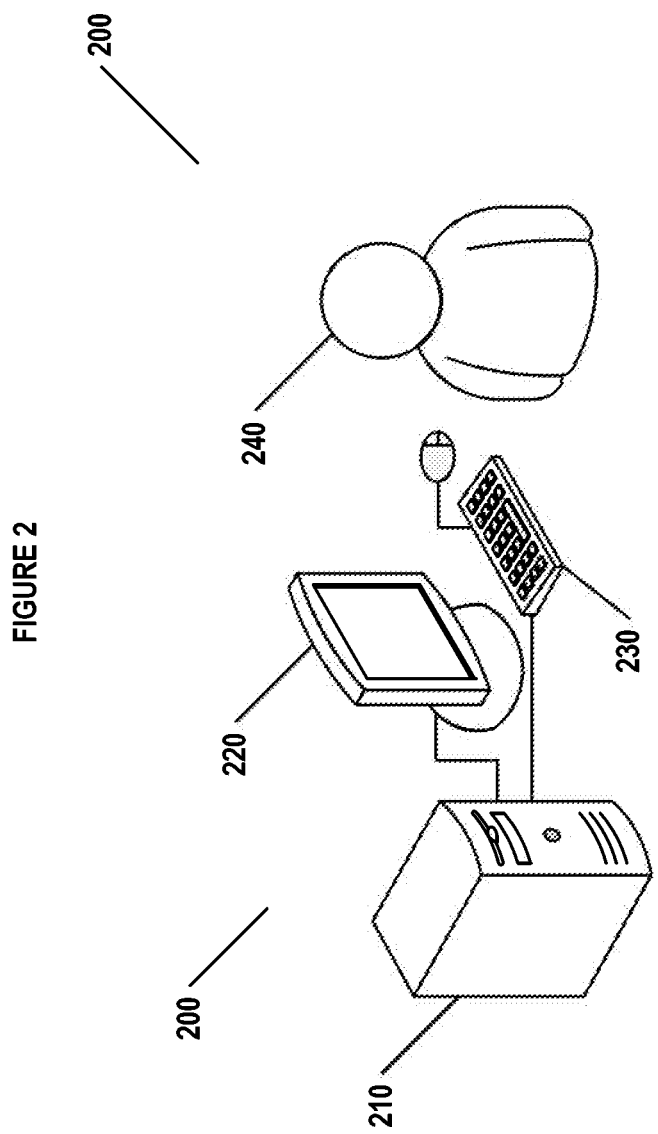
FIG. 2 illustrates an example system for occlusion estimation in dental prosthesis design.

FIG. 2 illustrates an example system 200 for occlusion estimation and/or prosthesis manipulation in dental prosthesis design. The system 200 may include one or more computers 210 coupled to one or more displays 220, and one or more input devices 230. An operator 240, who may be a dentist, dental technician, or other person, may plan dental prostheses using system 200 by manipulating the one or more input devices 230, such as a keyboard and/or a mouse. In some embodiments, while working on the dental plan, the operator 240 may view the dental plan and other related dental plan data on the display 220. The display 220 may include two or more display regions or portions, each of which displays a different view of the dental plan. For example, in some embodiments, the display 220 may show a semi-realistic 3D rendering of the dental plan, a localized abstraction of the dental plan, and/or a cross-sectional representation of the dental plan. Each of these displays or portions may be linked internally within a program and/or using data on computer 210. For example, a program running on a computer 210 may have a single internal representation of the dental plan in memory and the internal representation may be displayed in two or more abstract or semi-realistic manners on display 220.

In some embodiments, the operator 240 may be able to perform a command, such as select, move, manipulate, or make transparent, opaque, or invisible, on a particular substructure in the dental plan. The operator 240 may be able to perform this command by manipulating the input device 230, such as clicking with a mouse on a particular region of one of the abstract or semi-realistic versions of the dental plan displayed on the display 220.

In various embodiments, the computer 210 may include one or more processors, one or more memories, and one or more communication mechanisms. In some embodiments, more than one computer may be used to execute the modules, methods, blocks, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a two-dimensional ("2D") or 3D display and may be based on any technology, such as LCD, CRT, plasma, projection, etc.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Techniques for Occlusion Estimation and Dental Prosthesis Design

Figure 3B:
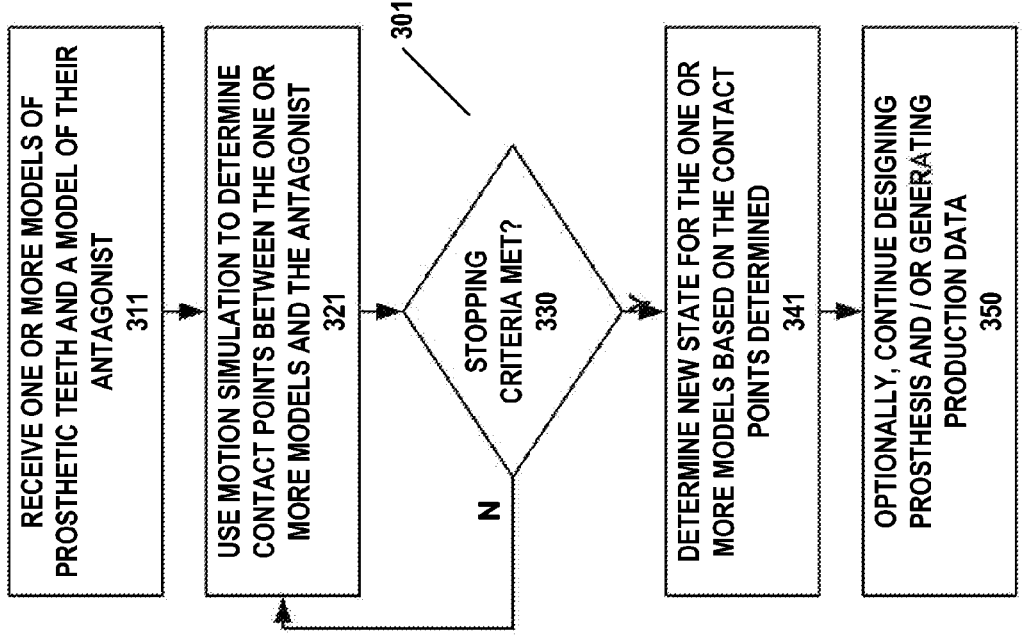
FIGS. 3A and 3B illustrate two example methods for occlusion estimation in dental prosthesis design.
Figure 3A:
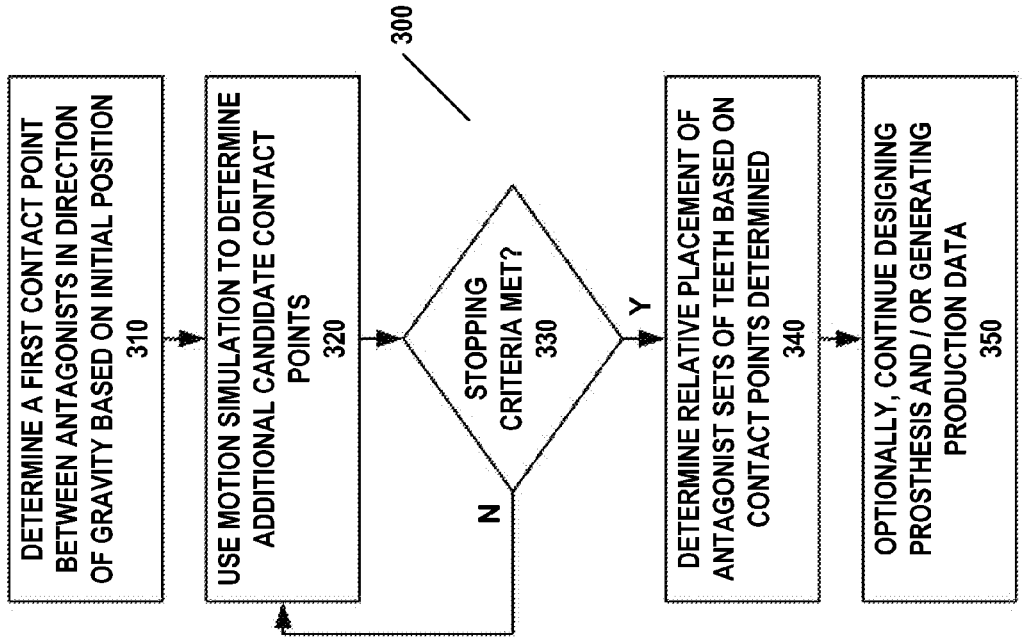

FIGS. 3A and 3B illustrate two techniques for occlusion estimation in dental prosthesis design. In estimating the occlusion, the technique may include motion simulation of one 3D model of teeth with respect to another 3D model of teeth. The motion simulation may include, in various embodiments, a six-degrees-of-freedom rigid body motion simulation, free-fall simulation, a rigid body simulation with one or a combination of constraints, or other motion simulation. The techniques can proceed by having either the upper or lower set of teeth be the 3D model that "moves" and the other be stationary. Alternatively, both models could move with respect to the others. The first step in occlusion estimation, in some embodiments, may include determining as a first contact point, the point on the lower 3D model which is closest, in the direction of gravity, to the upper 3D model. Once that initial contact point is determined, other candidate contact points between the upper 3D teeth model and lower 3D teeth model may be determined using simulated motion until one or more predetermined stopping criteria are met. In various embodiments, the initial contact point may be determined by finding the closest point between the first and second 3D models in the gravity direction. In subsequent steps of the motion simulation, candidate contact points (possibly including the initial contact point) may be found. After assessing the appropriateness of the candidate contact points, each candidate contact point (possibly including the initial contact point) may or may not be chosen for use in subsequent steps of the motion simulation. For example, if a particular contact point is determined, and it is between the initial contact point (assuming that the initial contact point was again found to be a contact point in this step of the simulation) and the center of gravity, the particular contact point may be used instead of the initial contact point. In this way, the first contact point may not be used in subsequent steps of the simulation and, similarly, may not end up in the final set of contact points that are used to define the occlusion between the first and second 3D models.

Figure 16:
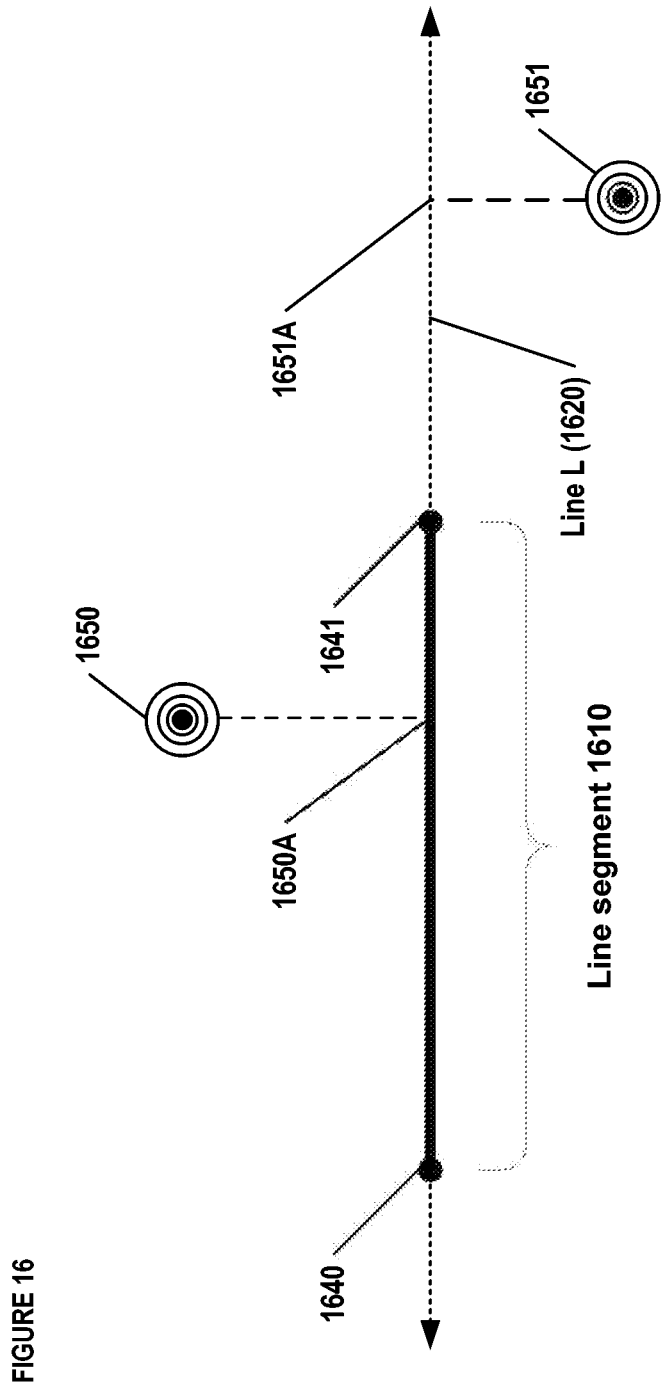
FIG. 16 depicts an abstract representation of the relative placement of contact points and the center of gravity.

In various embodiments, determining whether two contact points are on the opposite sides of the center of gravity may include defining a bisector or bisection plane through the center of gravity that splits the first 3D model into two segments, for example, a left segment and a right segment, and, optionally, splits the second 3D model into two segments, for example, the left segment and the right segment. For example, if the first 3D model of teeth includes all of the teeth in the lower jaw of a patient and the center of gravity is along the center line of the jaw, then the teeth on the left side of the mouth and the teeth in the right side of the mouth may be in different sections. Determining whether there are two contact points on the opposite sides of the center of gravity may include determining whether there are contact points in the two different sections of the mouth (the left section and the right section). As another example, consider FIG. 16. If two contact points define a line segment 1610, that is, from one contact point 1640 another contact point 1641, and the line segment 1610 is part of a line L 1620, then determining whether a center of gravity is between the two contact points may include determining whether the closest point on line L 1620 to the center of gravity is between the two contact points 1640 and 1641, or on the line segment 1610 defined by the two contact points 1640 and 1641. For an example center of gravity 1650, the closest point on the line segment 1610 is point 1650A. Since 1650A is between the two contact points 1640 and 1641, the center of gravity 1650 is considered "between" the two contact points. If on the other hand a center of gravity's 1651 closest contact point 1651A on line L 1620 is not on line segment 1610, then the center of gravity is not considered to be "between" the two contact points 1640 and 1641.

As another example, in some embodiments, when motion simulation is about a rotation axis (described elsewhere herein), checking to see whether the center of gravity is between two contact points comprises can include projecting the contact points onto the rotation plane (e.g., a plane whose normal is the rotation axis and that includes the gravity center on the plane). Various embodiments can then determine whether the projected points are on each side of a certain line defined by the projection of the gravity force vector onto the rotation plane and going through the gravity center. If the two are on opposite sides of the certain line, then they are on opposite sides of the center of gravity. There are numerous other ways to determine whether the center of gravity is between the two contact points, and these are considered within the scope of the embodiments herein.

Determining whether the center of gravity is within a triangle that is defined by three contact points may include projecting the triangle that is defined by the three contact points onto the occlusal plane and projecting the center of gravity onto the occlusal plane. If the center of gravity projected onto the occlusal plane lies within the triangle defined by the three contact points, then it may be considered that the center of gravity is within the triangle defined by the three contact points. As above, numerous other methods of determining whether the center of gravity is within the triangle defined by the three contact points may be used and are considered part of the embodiments herein.

In various embodiments, the techniques described herein may include changing the state (e.g., position, rotation, scaling, shape, etc.) of one or more 3D models based on the contact with the antagonist teeth. For example, if a crown or bridge is being designed and there are multiple units (e.g., teeth) in the crown or bridge, then each unit in the bridge or crown may be rotated, scaled, or otherwise changed in order to provide at least one contact point with the antagonist. After the relative placement of the occluding sets of teeth are determined based on the contact points or after new states for one or more 3D teeth models are determined based on the contact points, designing the prosthesis may continue and/or production data for the prosthesis may be generated based on the 3D model of the prosthesis.

Turning now to FIG. 3A, which depicts a method 300 for occlusion estimation in dental prosthesis design, in block 310 a first contact point is determined in the direction of gravity based on the initial positions of the 3D models of occluding teeth. As noted above, the initial position may be defined based on the known relative positions for the first 3D model and the second 3D model. For example, the initial position may be known because a scanning procedure to obtain the first 3D model of the teeth (e.g., the lower set of teeth) and the second 3D model of the teeth (e.g., the upper set of teeth) may have been performed and the initial placement may be defined in the relative placement of the first 3D model and the second 3D model during the scanning procedure. This may happen if both 3D models are placed in known relation to each other during the scanning procedure or if each of them is placed relative to some fixed coordinate system during the scanning procedure. In some embodiments, the initial relative placement of the first 3D model with respect to the second 3D model of the teeth may be known based on a scanned check bite. That is, if the second 3D model of the teeth is determined at least in part based on the scanned check bite, then the first 3D model of the teeth may be surface matched to the check bite and that check bite may provide the initial placement of the two sets of teeth. Additionally, as noted above, an operator may manipulate the relative placement of the first 3D model and the second 3D model before performing the occlusion estimation.

Returning again to block 310, determining the first contact point between occluding teeth in the direction of gravity based on the initial position may also include an initial determination of the gravity direction. The gravity direction may be determined in any of numerous ways, including having it be predefined based on the scanning procedure and the like. Additionally, the gravity direction may be perpendicular to an occlusal plane of the first and/or the second 3D model of teeth. The occlusal plane of the two 3D models may be known ahead of time or it may be determined in any number of ways. For example, if a planar object such as a rectangle is "dropped" onto, e.g., the first 3D model, (or vice versa) then that rectangular object, once it has come to rest on the first 3D model, may define the occlusal plane. "Dropping" the rectangular object onto the 3D model may be accomplished using, e.g., the simulated motion described with respect to FIG. 3A or FIG. 3B, or any other appropriate technique. The normal of the planar rectangular object may be used to define the direction of gravity. In various embodiments, the distance between the first and second 3D models is determined in a direction other than the direction of gravity. For example, the overall closest point between two triangular meshes representing the first and second 3D models may be determined or the closest point between the two 3D models in a direction other than gravity may be determined and used as the closest point between the 3D models.

Determining the first contact point between the occluding sets of teeth in the direction of gravity in block 310 may be performed based on any appropriate calculation. For example, it may be determined by performing a numerical calculation of the closest point between the two 3D models in the direction of gravity. In some embodiments, the closest point between the two 3D models may be determined by simulating free fall of one of the 3D models with respect to the other 3D model. For example, based on the initial position, one of the 3D models may be "dropped" onto the other 3D model. The first contact point between the two 3D models when dropped may be the closest point between the two 3D models. One 3D model may then, optionally, in some embodiments, be moved toward the other in the direction of gravity so that the closest point between the two 3D models would be the contact point between the two 3D models. Similarly, in some embodiments, the two 3D models may then, optionally, be moved toward each other in the gravity direction instead of moving one 3D model and keeping one fixed.

In block 320, motion simulation may be used to determine subsequent candidate contact points. After the first contact point is determined, it is used as a constraint on the simulated motion. That is, that contact point will remain in contact for the duration of that step of the simulated motion. The simulated motion will result in the moving 3D model pivoting around that contact point until one or more other contact points are determined. In some embodiments, it is possible that one or more contact points may be lost, perhaps due to numerical error. If one or more contact points are lost due to numerical error, the simulation may continue. For example, the moving 3D model could fall in the gravity direction until at least one contact point is found.

Determining a contact point may include using any particular type of collision detection. For example, if the first and second 3D models each are represented as a triangular mesh, then contact points may be determined by looking for collisions between the two triangular meshes. Further, in some embodiments, if it is determined that two particular triangles, one in each 3D model's triangular mesh, intersect, then the actual point or edge of intersection may be used (e.g., if it is known) or if there is merely an indication that the two triangles intersect, then the contact points may be estimated as the centers of the two triangles. Numerous other collision detection techniques may be used to determine contact points and are encompassed by embodiments herein.

Once the candidate' contact points are determined, a check will be made in block 330 to determine whether the stopping criteria have been met. Checking the stopping criteria may include determining whether two contact points in the set of candidate contact points are on opposite sides of the center of gravity. Another check of stopping criteria may include determining whether there are three contact points which define a triangle that includes the center of gravity of the moving 3D model.

If the stopping criteria are not met, then a determination may be made as to which contact points to use in subsequent steps of the motion simulation (executed in block 320). For example, consider FIGS. 9A and 9B. The previous set of candidate contact points may have already included contact points 940 and 941 in FIG. 9A, and those two contact points 940 and 941 and an additional contact point 942 may have been determined. Since contact points 940, 941, and 942 do not form a triangle that encompasses the center of gravity 950, a determination may be made as to which of the candidate contact points 940, 941, and/or 942 to use in subsequent motion simulations. The three contact points define three axes of rotation 961, 960, and 962. These axes of rotation may be used in a motion simulation to determine whether the other contact points should be included in the subsequent step of the motion simulation. For example, the contact points 940, 941 may have an axis of rotation 960 associated with them. Turning to FIG. 9C, if axis of rotation 960 is used during a motion simulation, the normal force 998 applied on the moving object during the motion simulation on the other candidate contact point 942 will be against the force 999 associated with the simulated rotation 960. The point 942 being on the same side of the center of gravity 950 would normally rotate during motion simulation. Yet, the contact point 942 is already in contact with the other 3D model and therefore further rotation (or dropping) will not be possible. As such, axis of rotation 960 will be excluded from consideration as the proper axis of rotation. Therefore, the set including both candidate contact points 940, 941 will not be used in the subsequent step of the simulation. If, on the other hand, the simulation were performed with axis of rotation 961, which bridges candidate contact points 941, 942, then as the moving 3D model is in motion, the normal force on candidate contact point 940 will create a moment in the direction of rotation. Therefore, the axis of rotation 961 between candidate contact points 941, 942 is a proper axis of rotation. Therefore, candidate contact points 941, 942 will be used in the subsequent step of the motion simulation.

Figure 9B:
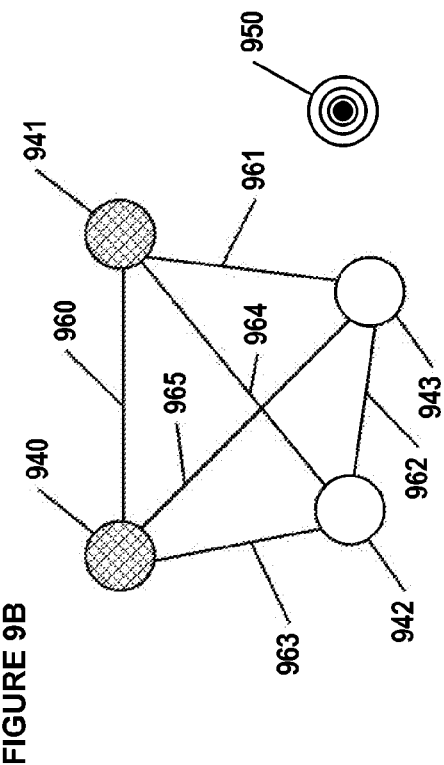
FIGS. 9A, 9B, and 9C illustrate two sets of candidate contact points for occlusion estimation in dental prosthesis design.
Figure 9A:
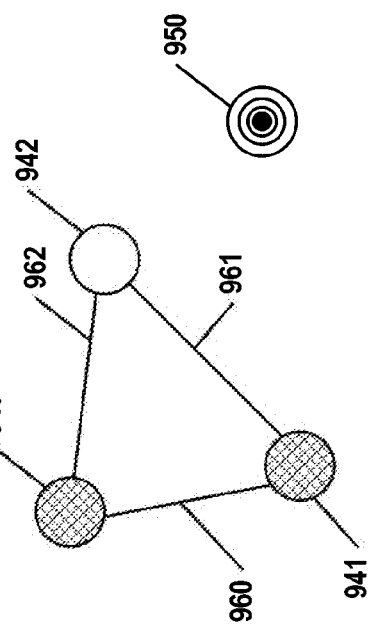
Figure 9C:
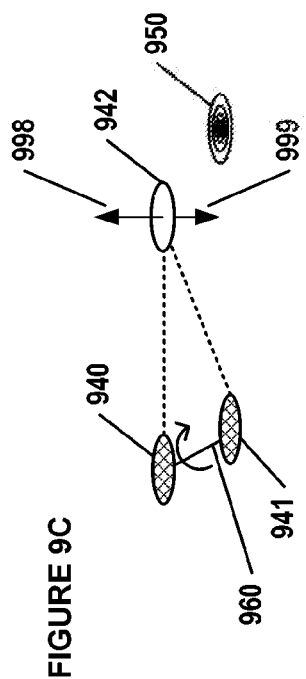

As another example, in FIG. 9B, if there are four candidate contact points 940, 941, 942, and 943, then there may be six candidate axes of rotation 960-965. Performing a similar analysis as that described above, candidate axes of rotation 960, 962, 963, 964, and 965 will all be eliminated because a normal force on one of the candidate contact points 940-943 will be against the axis of rotation. Only the candidate axis of rotation 961 will have no candidate contact points with force normals create moments in the opposite direction of rotation. Therefore, the candidate contact points 941 and 943 will be used in the subsequent simulation step.

If the stopping criteria are met in block 330, then in block 340 the relative placement of the occluding sets of teeth may be determined based on the contact points. In some embodiments, the relative placements of occluding teeth may be known based on the contact points and no further calculation may be needed to determine the relative placements. In various embodiments, determining the relative placements of the occluding sets of teeth may include recording a matrix, quaternion, or other transformation of the 3D models of occluding teeth after the contact points have been determined. The contact points may define the relative placement of the two 3D models with respect to one another. The two 3D models may be translated, rotated, or a transformation between the two 3D models may be stored. In block 350, the design of the prosthesis may be continued or data may be generated for production of the prosthesis. Designing dental prostheses may be performed using any appropriate system, methods, or techniques, such as those described in U.S. patent application Ser. No. 12/703,601, filed Feb. 10, 2010, entitled Dental Prosthetics Manipulation, Selection, and Planning, which is hereby incorporated by reference in its entirety for all purposes.

FIG. 3B illustrates another method 301 of occlusion estimation for dental prosthesis design. In method 301, one or more 3D models of prosthetic teeth and the 3D model of their antagonist may be received in block 311. For example, looking to FIG. 7, an antagonist 730 may be received, in addition to 3D models of individual prosthetic teeth 770, 771, and 772. Together these may be used to design a crown or a bridge that is defined by the 3D models of the prosthetic teeth 770, 771, and 772. Additionally, as part of block 311, an initial position of the one or more 3D models of prosthetic teeth and the 3D model of their antagonist may be received or determined. For example, an operator may initially place the teeth with respect to the antagonist, or the teeth in the antagonists' relative placement may be algorithmically determined or known based on the scanning procedure used to obtain the 3D model (described elsewhere herein).

After the 3D models have been received in block 311, contact points between each of the one or more 3D models of prosthetic teeth and the antagonist may be determined in block 321. Determining the contact points between the one or more 3D models and the antagonists may include rotating about an axis, simulating motion, manipulating the size, translation, rotation, or orientation of the 3D models until a contact point is determined, and the like. Returning again to FIG. 7, block 321 may, in some embodiments, include determining contact points 740, 741, and 742 by rotating the 3D models 770, 771, and 772 and/or simulating motion of the 3D models 770, 771, and 772. For example, 3D models 770, 771, and 772 may have a shared axis 755. After a first contact point is determined for each of the 3D models 770, 771, and 772, these first contact points, along with shared axis 755, may define the axes about which to rotate each of 3D models 770, 771, and 772 (e.g., the axis about which to rotate a 3D model may be defined as an axis through the contact point, parallel to shared axis 755). Simulated motion can continue as part of block 321 until two contact points are determined that are on opposite sides of the center of gravity, which is assessed in block 330 (e.g., similar to the method 300). After the one or more contact points have been determined in block 321, then, in block 330, stopping criteria may be checked.

The stopping criteria may include the determination of a single contact point or the determination of multiple contact points as described above with respect to method 300. As discussed above, in some embodiments, multiple contact points may be determined for each of 3D models 770, 771, and 772. In various embodiments, as part of method 301, two or more contact points are determined for each of 3D models 770, 771, and 772 that represent posterior teeth and only a single or first contact point is determined for each 3D model 770, 771, and 772 that represents anterior teeth. For example, each 3D model 770, 771, and 772 that represents anterior teeth may be translated in the gravity direction in order to find the closest contact point (in block 321) and this may meet the stopping criteria (block 330) for that 3D model.

In some embodiments, the one or more 3D models of prosthetic teeth may be expanded or contracted until there is a single contact point (or multiple contact points). This expansion or contraction can continue until the stopping criteria are met (e.g., determining the requisite number of contact points). The expansion or contraction may also be followed by motion simulation. In some embodiments, each of the individual one or more prosthetic teeth will have a separate simulated motion (e.g., without the constraints of the axis 755 shown in FIG. 7). The separate simulated motion of each of the 3D models (e.g., 3D models 770, 771, and 772) may be performed in a manner similar to that described in with respect to method 300.

After the predetermined stopping criteria have been met as determined in block 330, then, in block 341, the new state for the one or more 3D models based on the contact point may be determined. The new state may be the new position, rotation, orientation, size, and/or shape of the one or more 3D models of the prosthetic teeth. After the new state has been determined in block 341, then, optionally, the operator may continue designing the prosthesis or may generate production data for the prosthesis (block 350).

Other methods and techniques may be used. Further, other blocks may be added to each of methods 300 and 301, or the blocks may be executed in a different order, may be executed simultaneously, or may be left out altogether. For example, a method may commence by performing a motion simulation, thereby skipping block 310 and proceeding directly to block 320. In such a simulation, the first contact point will be determined by free fall of one 3D model onto the other and then subsequent contact points may be determined in block 320 until the predetermined stopping criteria are met in block 330. Then the relative placement on the occluding sets of teeth based on the contact points may be determined in block 340. In various embodiments, the stopping criteria may include there being no further movement in the motion simulation. For example, the simulation of motion may continue until the two 3D models are in a static position, one with respect to the other. Various other embodiments are also considered within the scope herein.

Other Embodiments

Figure 4:
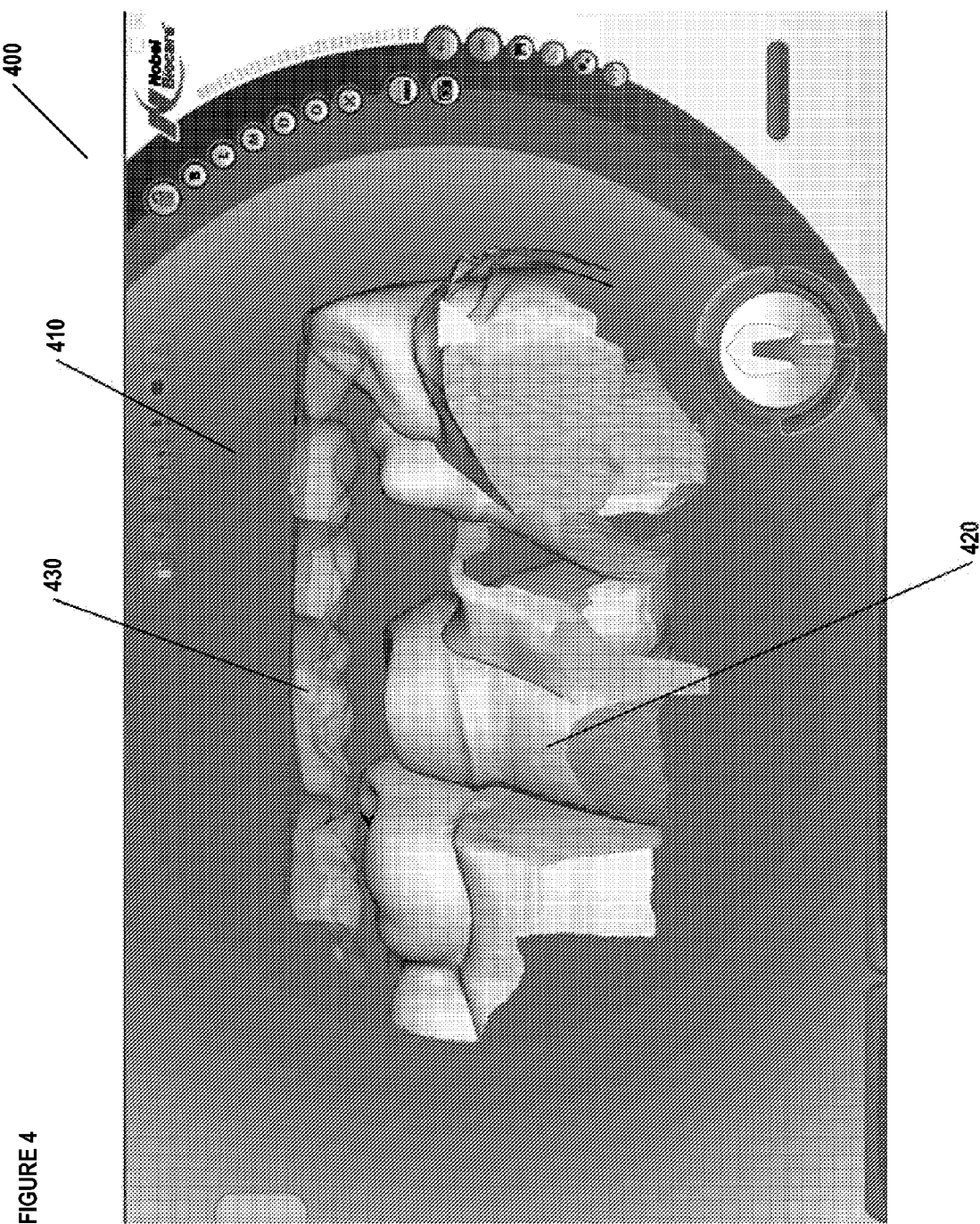
FIG. 4 illustrates a third interface for occlusion estimation in dental prosthesis design.
Figure 5:
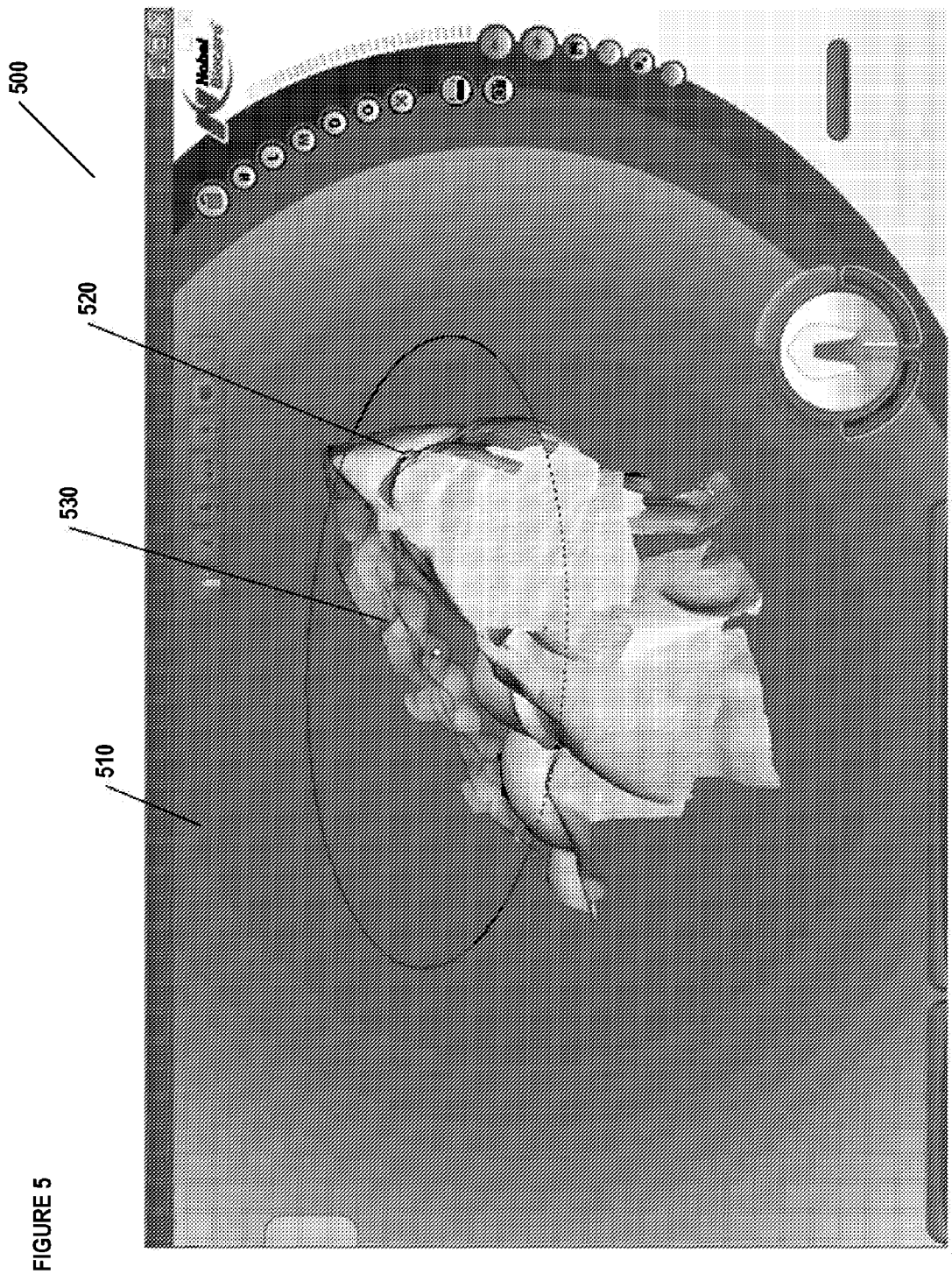
FIG. 5 illustrates a fourth interface for occlusion estimation in dental prosthesis design.
Figure 6:
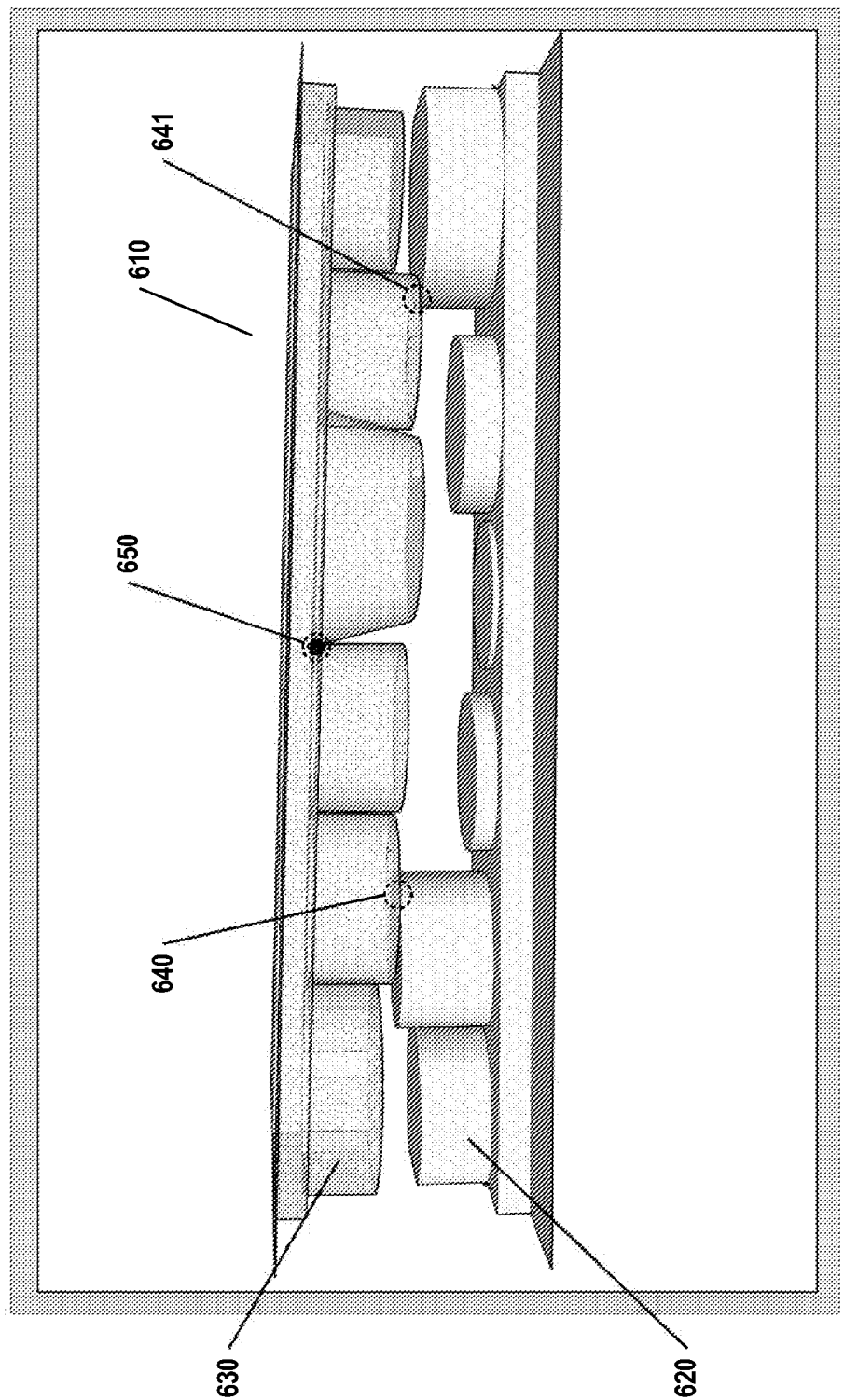
FIG. 6 illustrates a fifth interface for occlusion estimation in dental prosthesis design.

FIG. 4 illustrates an interface 400 with an overlaid representation portion 410 that depicts a lower teeth model 420 and an upper teeth model 430. As depicted in the figure, there may initially be a gap between the lower teeth model 420 and the upper teeth model 430. In some embodiments, as depicted in FIG. 5, which illustrates an interface 500 with an overlaid representation portion 510, having three contact points on an approximately linear set of upper and lower teeth models (e.g., 520, 530) may cause the 3D models to "fall" in a way that is undesirable or anatomically impossible. As depicted in FIG. 5, 3D model 530 has fallen onto 3D model 520 and has tilted in a way that would not be possible given the constraints of the human jaw. In such situations, it may be desirable to have a stopping criterion that includes looking for two candidate contact points that are on opposite sides of a center of gravity. FIG. 6 illustrates an interface 600 with an overlaid representation portion 610 in which an upper teeth model 630 dropped onto a lower teeth model 620 using motion simulation. In FIG. 6, the stopping criterion (a) used to determine the relative placement of the lower teeth model 620 and the upper teeth model 630 may include determining two candidate contact points 640 and 641 that are on the opposite side of the center of gravity 650. In comparing FIGS. 5 and 6, it may be seen that, in some circumstances, use of this two-point stopping criterion may produce better results than a three-point stopping criterion.

Figure 7:
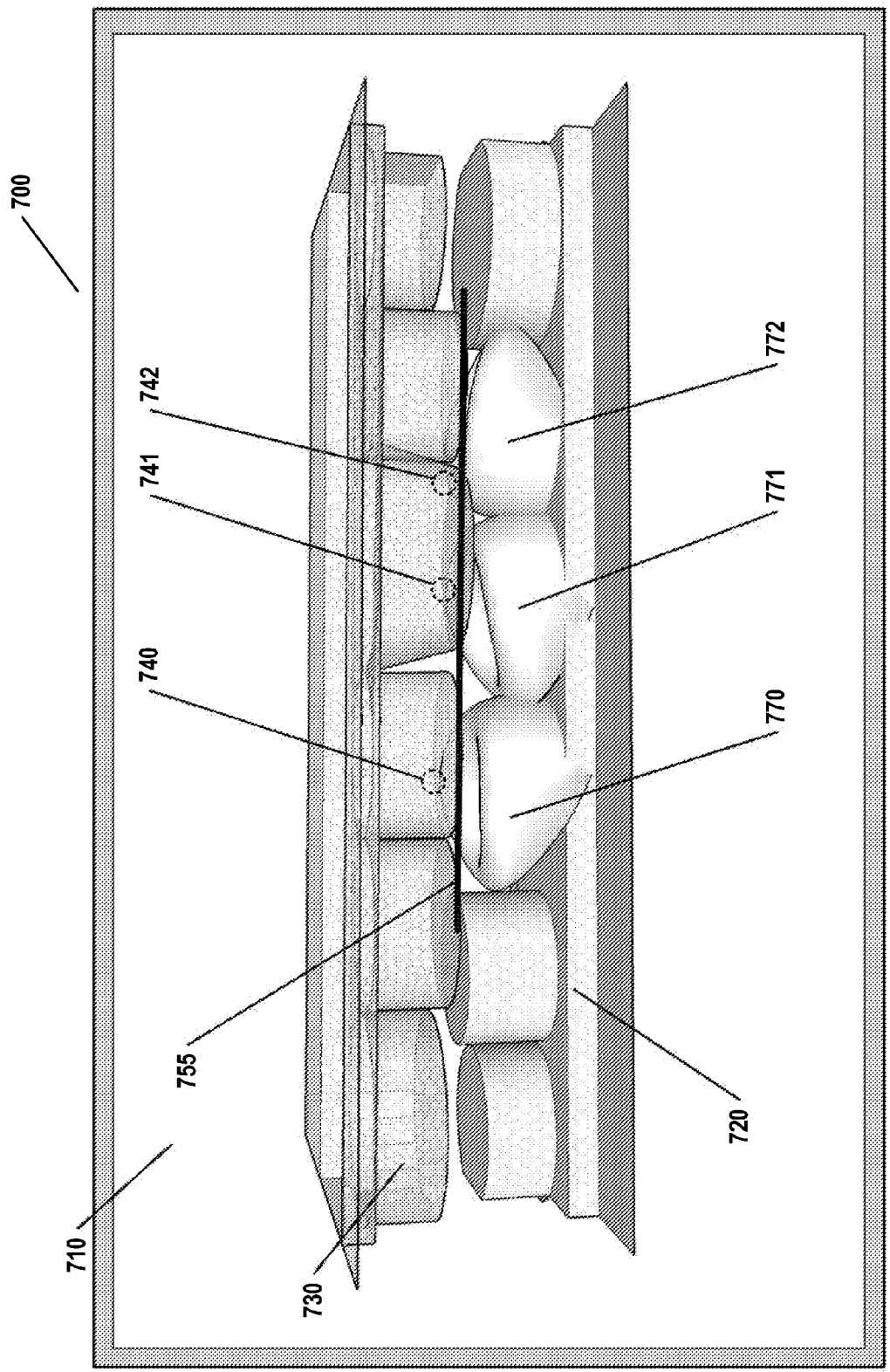
FIG. 7 illustrates a sixth interface for occlusion estimation in dental prosthesis design.
Figure 8:
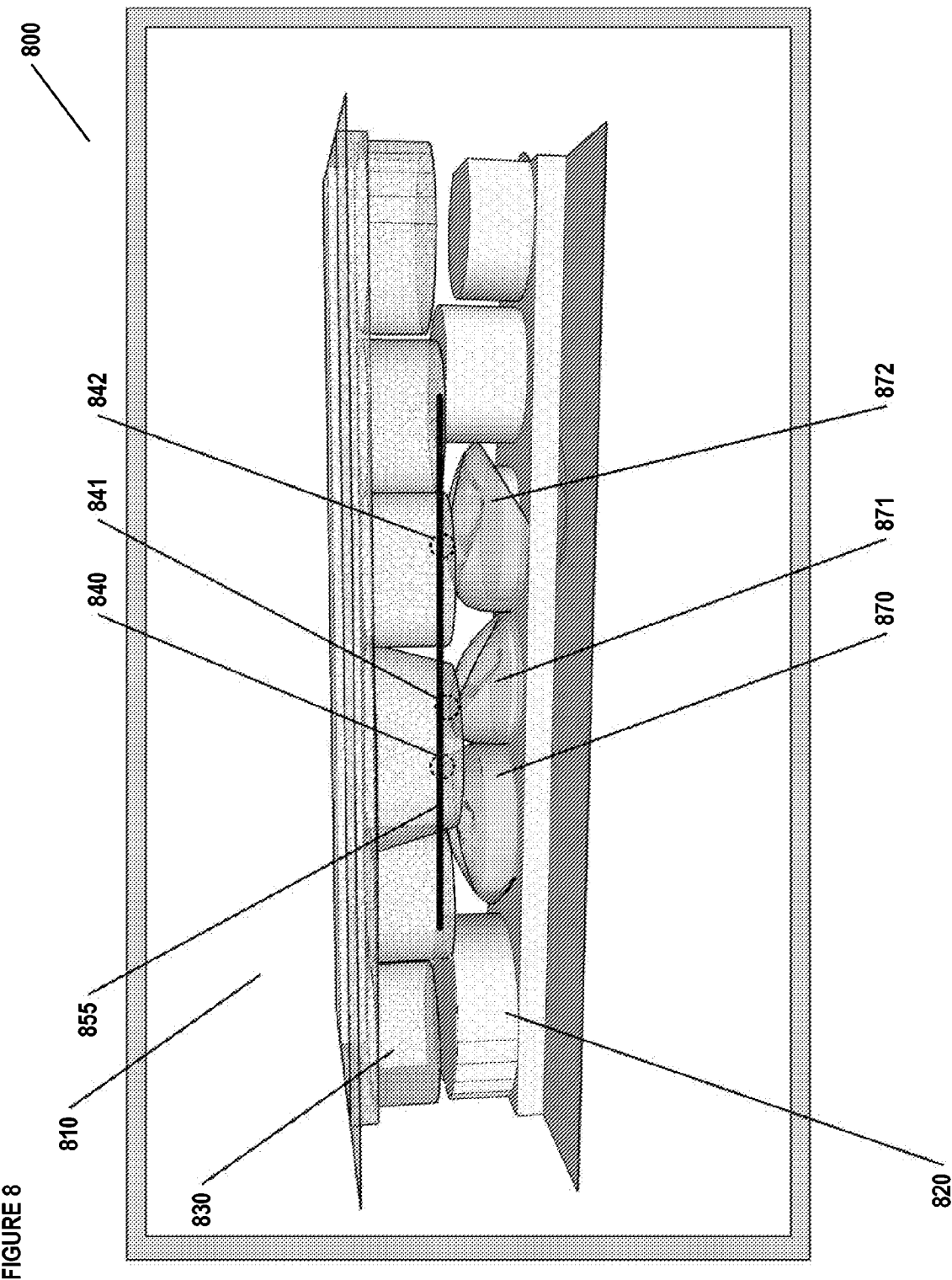
FIG. 8 illustrates a seventh interface for occlusion estimation in dental prosthesis design.

FIGS. 7 and 8 depict multiple 3D models of individual prosthetic teeth being moved with respect to an antagonist. FIG. 7 is described above. FIG. 8 illustrates an interface 800 that includes an overlaid representation portion 810. The overlaid representation portion 810 illustrates the movement of 3D models of individual prosthetic teeth 870, 871, and 872 with respect to an antagonist 830. The interface also shows a lower teeth model 820. Interface 800 also illustrates a shared axis of rotation 855 for the 3D models of the individual prosthetic teeth 870, 871, and 872. In some embodiments, as described herein, performing motion simulation of the individual 3D models of the prosthetic teeth 870, 871, and 872 may include allowing those prosthetic teeth to rotate about axes parallel to axis 855 (as described above with respect to shared axis 755) in the direction corresponding to gravity until contact points 840, 841, and 842 are determined. In some embodiments, two contact points will be determined for each tooth, e.g., one on each side of the gravity center for the tooth (described above). In other embodiments, not depicted in FIG. 8, if there is no axis of rotation 855, then each of the individual prosthetic teeth may have simulated motion performed, may be scale translated, rotated, or otherwise modified until contact points are determined, or any other appropriate technique may be used. Further, in some embodiments, the collision detection or other techniques may be used to ensure that neighboring teeth do not overlap or otherwise have intersecting volumes. Examples of this are described elsewhere herein.

Figure 10:
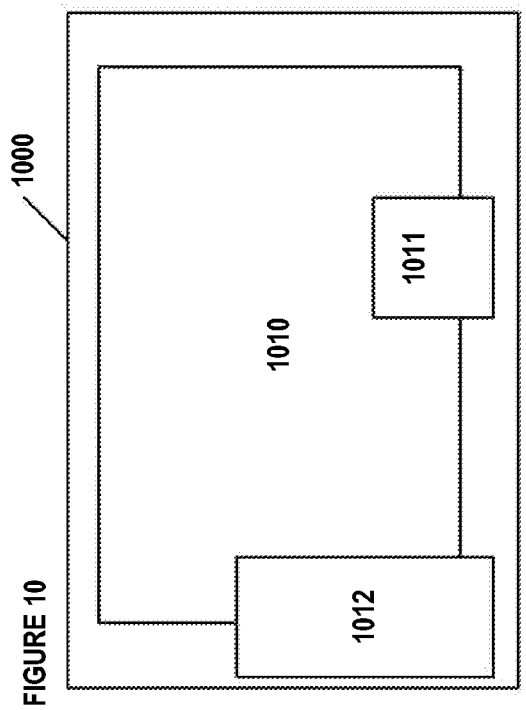
FIG. 10 illustrates an eighth interface for occlusion estimation in dental prosthesis design.
Figure 11:
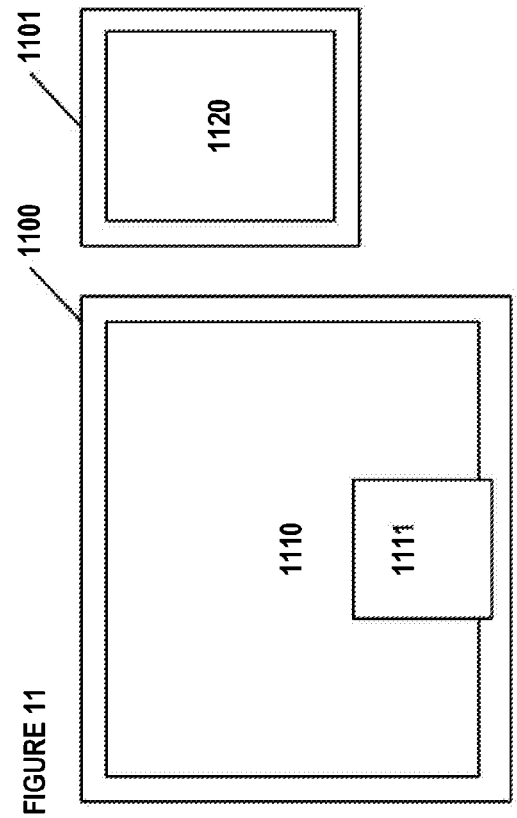
FIG. 11 illustrates a ninth interface for occlusion estimation in dental prosthesis design.

Various of the embodiments herein show interfaces of a certain configuration. Other configurations of interfaces are also possible. Turning to FIG. 10, it is possible that an interface 1000 can have an overlaid representation portion 1010, a global selection portion 1011, and a distance map portion 1012, all on a single interface 1000. It is also possible, as depicted in FIG. 11, that two separate sub-interfaces 1100 and 1101 may be used. The distance map portion 1120 may be on interface portion 1101 and the overlaid representation portion 1110 and global selection portion 1111 may be on interface portion 1100. These various interface portions may be shown on separate screens, on separate displays or in separate windows. Other configurations of the various portions on various displays or in various windows may also be used.

Prosthesis Manipulation in Dental Prosthesis Design

Figure 12:
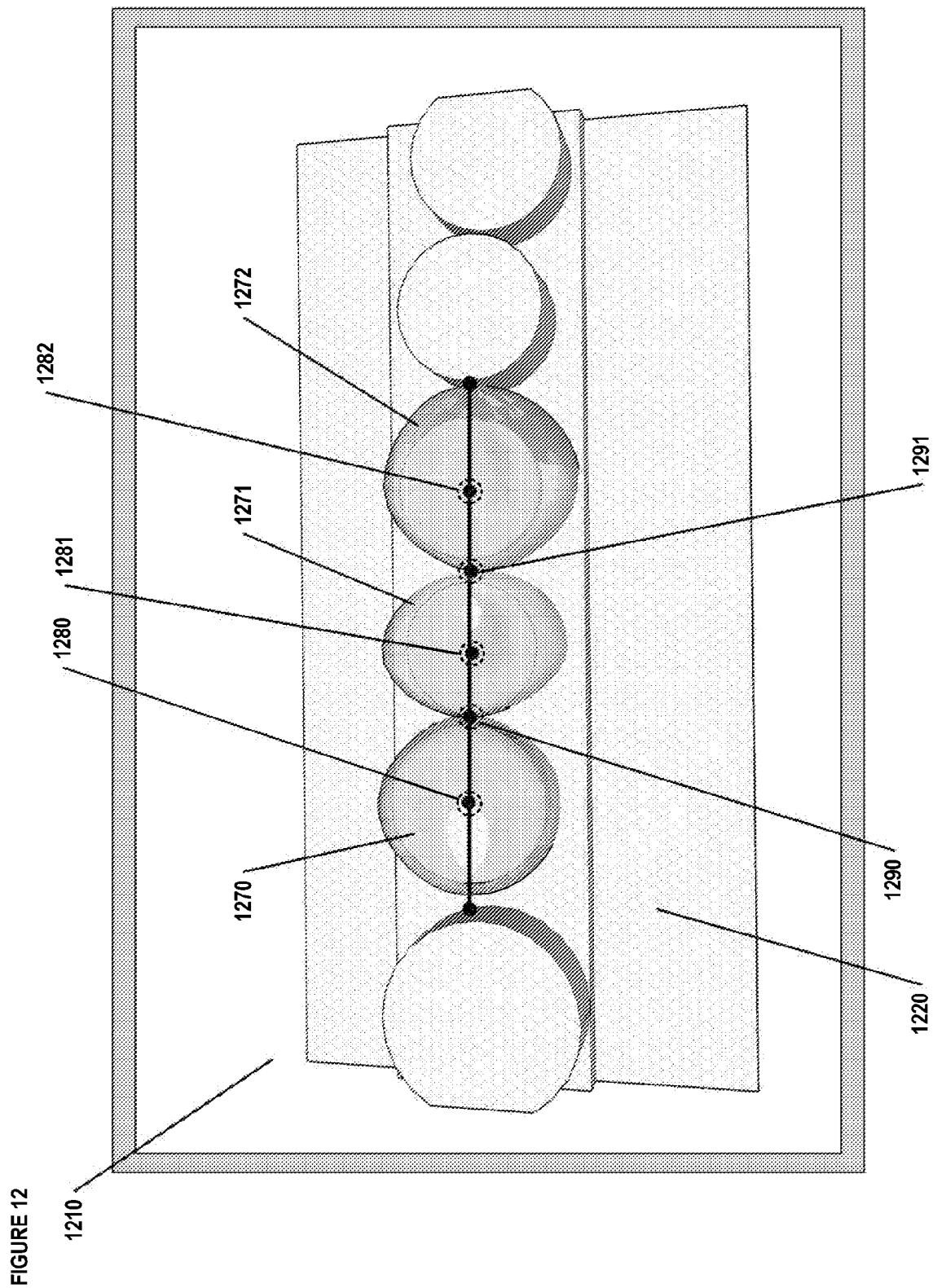
FIG. 12 illustrates a first interface for prosthesis manipulation in dental prosthesis design.
Figure 14A:
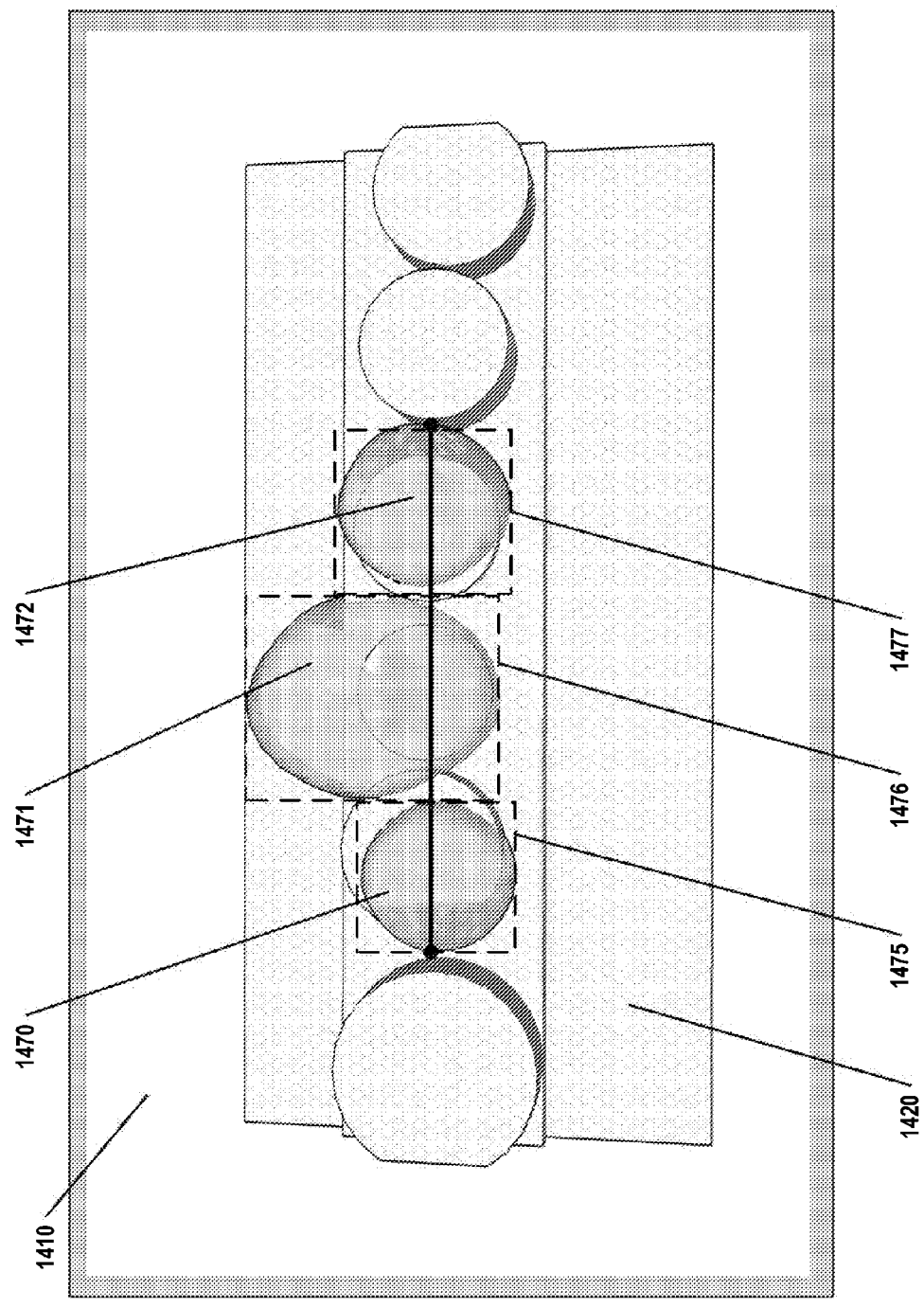
FIGS. 14A and 14B illustrate two interfaces for prosthesis manipulation in dental prosthesis design.
Figure 14B:
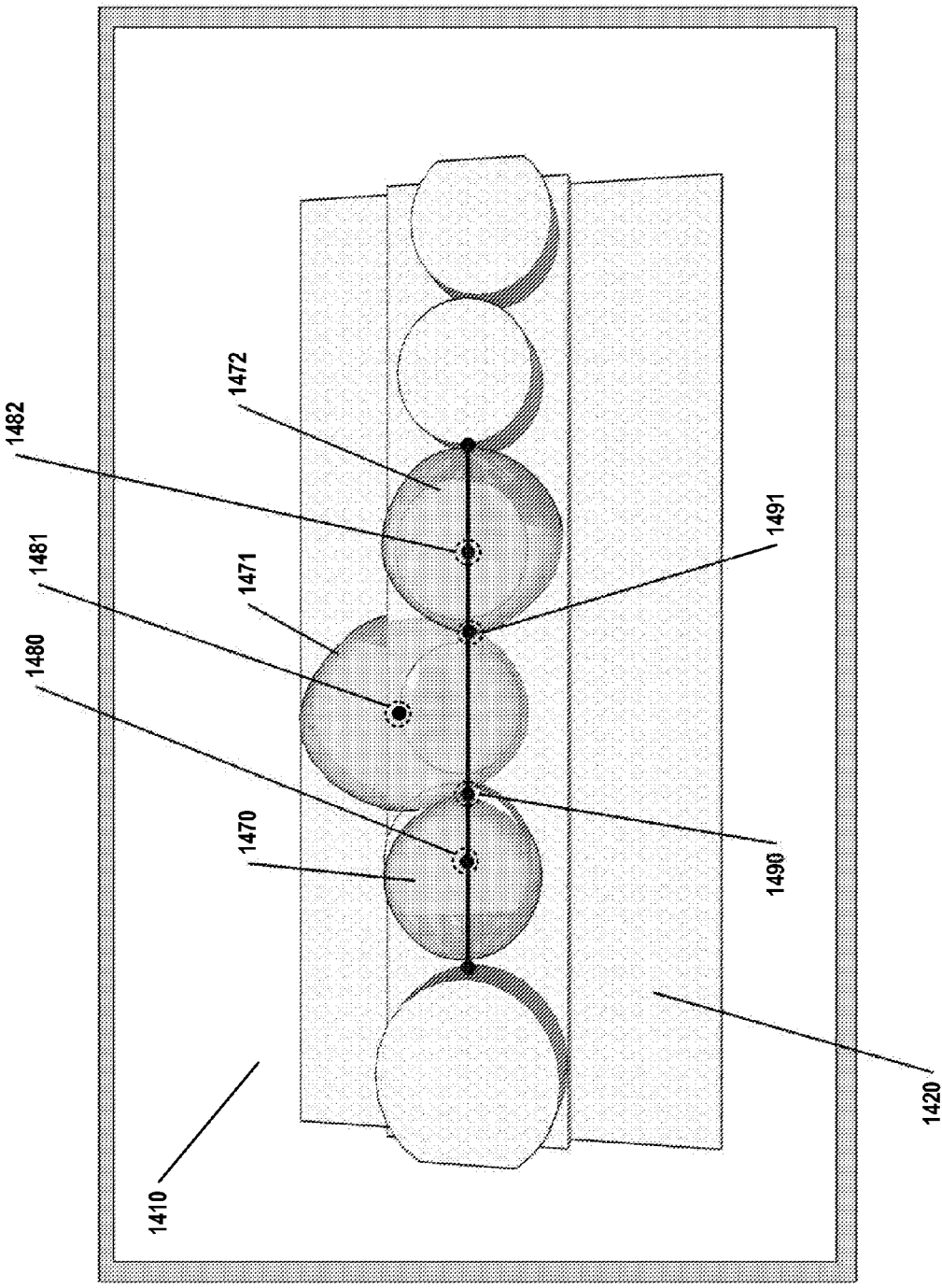

As discussed above, when designing a virtual multi-tooth prosthesis, the operator may move 3D models of individual prosthetic teeth independently of one another. Consider, for example, FIG. 12. FIG. 12 depicts an interface 1200 which has an overlaid representation portion 1210. In the overlaid representation portion 1210, there is a 3D model of lower teeth 1220 which is shown as opaque, as well as 3D models of prosthetic teeth 1270, 1271, and 1272. Also depicted in FIG. 12 are manipulation handles 1280, 1281, 1282, 1290 and 1291. These manipulation handles may provide a number of ways to manipulate the individual 3D models of the prosthetic teeth 1270, 1271 and 1272 with respect to one another, with respect to the model of the lower teeth 1220, and/or with respect to a virtual multi-tooth prosthesis encompassing the 3D models of prosthetic teeth 1270, 1271 and 1272. That is, if there were a 3D model of a virtual multi-tooth prosthesis that included the 3D prosthetic teeth 1270, 1271 and 1272, then the manipulation points 1280, 1281, 1282, 1290 and 1291 may allow the models for 3D prosthetic teeth 1270, 1271 and 1272 to be manipulated with respect to the virtual multi-tooth prosthesis. Examples of manipulations that may be available via the manipulators 1280, 1281, 1282, 1290 and 1291 may be scaling, translating, rotating, etc. For example, if an operator were to use manipulator 1290 and were to shift it left (in the orientation shown in FIG. 12), then the 3D model of prosthetic tooth 1270 may decrease in size (e.g., be scaled smaller), and 3D model of prosthetic tooth 1271 may increase in size (e.g., be scaled larger). This is depicted in FIG. 14B, in which the manipulator 1490 has been moved to the left with respect to the location of manipulator 1290 in FIG. 12, and the 3D model of a prosthetic tooth 1470 has decreased in size as compared with 3D model of prosthetic tooth 1270 in FIG. 12. The 3D model of the prosthetic tooth 1471 has increased in size as compared with 3D model of prosthetic tooth 1271 in FIG. 12. Returning again to FIG. 12, if a different manipulator is moved by the operator, for example, manipulator 1281, then the tooth associated with that manipulator may be translated with respect to the other teeth or with respect to the virtual multi-tooth prosthesis. Looking again to FIG. 14B, we see that manipulator 1481 has been moved up in screen space with respect to where it was in FIG. 12. Therefore, the 3D model of the prosthetic tooth 1471 has been translated up in screen space with respect to the other teeth for the virtual multi-tooth prosthesis.

Other manipulators and manipulations are also possible and considered part of the scope of embodiments discussed herein. In various embodiments, other types of manipulations of the teeth are also possible. For example, there may be a manipulator (not depicted in FIG. 12) that would allow the operator to rotate an individual prosthetic tooth 1270, 1271 or 1272 around, for example, the coronal-apical axis and/or the distal-mesial axis. Other rotations may also be possible. In various embodiments, the manipulations may also include surface deformations, and the like.

Techniques for Prosthesis Manipulation in Dental Prosthesis Design

Figure 13B:
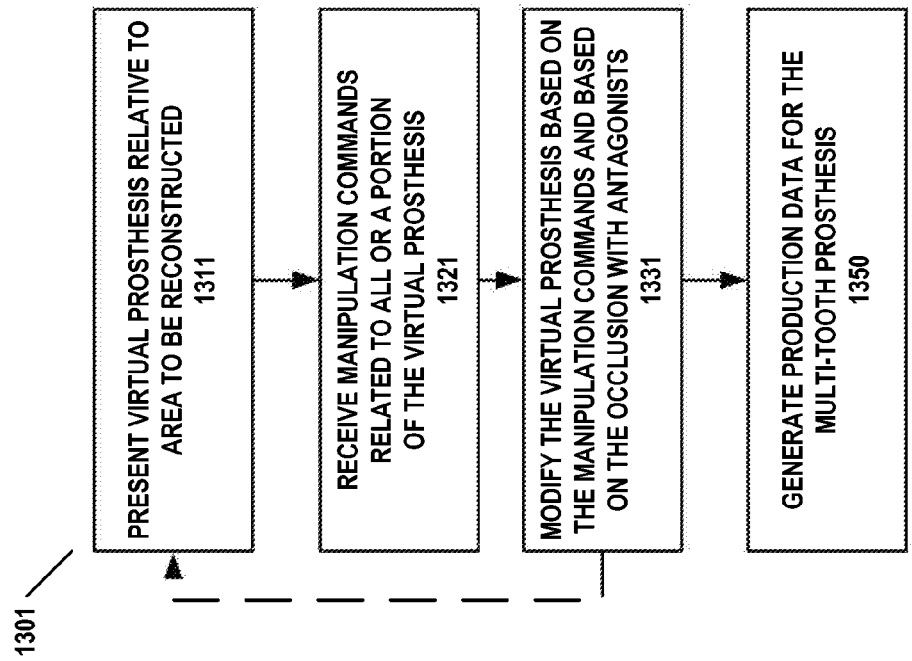
FIGS. 13A and 13B illustrate two example methods for prosthesis manipulation in dental prosthesis design.
Figure 13A:
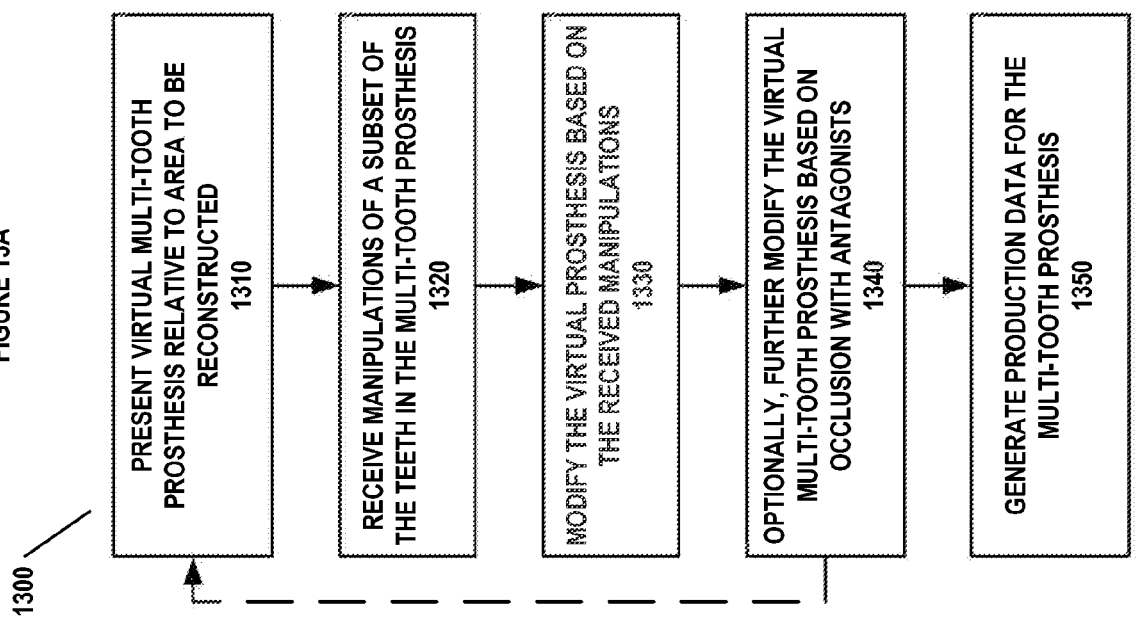

FIG. 13A depicts a method 1300 for prosthesis manipulation in dental prosthesis design. In block 1310, a virtual multi-tooth prosthesis is presented relative to an area to be reconstructed. For example, looking to FIG. 12, a virtual multi-tooth prosthesis including 3D models of prosthetic teeth 1270, 1271 and 1272 is presented relative to both the underlying portion that is to be reconstructed, as represented by lower teeth model 1220, as well as with respect to its antagonist teeth (not shown in FIG. 12).

In block 1320, a manipulation command is received, said manipulation command relating to a subset of the teeth in the virtual prosthesis. As used herein, the phrase "subset of the teeth in the virtual prosthesis" includes its customary and ordinary meaning, including meaning that the subset is fewer than all of the teeth in the virtual prosthesis, including one tooth in the virtual prosthesis. For example, looking again to FIG. 12, a manipulation command may be received related to a single 3D model of a prosthetic tooth 1270 or with respect to multiple models of prosthetic teeth 1270, 1271, and 1272. For example, a command relating only to a single 3D model of a tooth 1270 may be a translation manipulation indicated by the movement of manipulator 1280. This manipulation command may affect only the 3D model of prosthetic tooth 1270, as discussed more below, it may also affect, perhaps to a lesser extent, the position, scaling, placement, etc. of other 3D models of prosthetic teeth 1271 and 1272. The manipulation of manipulator 1290, which indicates a scaling of the 3D model of prosthetic teeth 1270 and 1271 relative to the virtual multi-tooth prosthesis and/or relative to one another, may affect those teeth and, perhaps to a lesser extent, the other 3D model(s) of prosthetic teeth 1272.

Returning again to FIG. 13A, block 1330 includes modifying the prosthesis based on the received manipulation commands. Modifying the teeth based on the received manipulation commands may include any appropriate action. For example, if the manipulation command is meant to translate a single 3D model of a tooth in the lingual or buccal direction, then that tooth may be translated in the lingual or buccal direction with respect to the other teeth and/or with respect to the virtual prosthesis. If the command received requires scaling of two or more of the teeth with respect to one another or with respect to the virtual multi-tooth prosthesis, then the 3D models of those teeth may be scaled appropriately. That is, in some embodiments, one of the teeth may be scaled to increase its size and the other may be scaled to decrease its size. Scaling the teeth with respect to one another in this way may prevent large gaps from forming in the multi-tooth prosthesis and/or prevent overlap between neighboring teeth.

Modifying the prosthesis based on the received manipulations (in block 1330) may include performing the requested action and, in some embodiments, performing additional actions or calculations in order to align or place all of the 3D models of teeth in the prosthesis and/or reduce gaps (or correct overlaps) between neighboring teeth. For example, in some embodiments, when neighboring teeth are scaled or translated, a gap may form between two teeth, as depicted in FIG. 15A. The gap depicted in FIG. 15A may have resulted, for example, from a scaling of the 3D model of prosthetic tooth 1570 with respect to the 3D model of prosthetic tooth 1571 or it may have resulted from translating either 3D model of prosthetic tooth 1570 and/or 3D model of prosthetic tooth 1571 with respect to one another.

In some embodiments, the techniques may include calculating the relative placement of all of the 3D models of prosthetic teeth in the virtual multi-tooth prosthesis after each manipulation command (or possibly after a series of manipulation commands). For example, after the manipulation command is received, all of the 3D models of the prosthetic teeth may be placed next to one another in the area to be reconstructed using bounding volumes as a first approximation. After the initial placement, the gaps (or overlaps) of the 3D models of the prosthetic teeth may be reduced or eliminated using the techniques described elsewhere herein. For example, looking to FIG. 14A, we see that the 3D models of prosthetic teeth 1470, 1471, and 1472 are bounded by bounding boxes 1475, 1476, and 1477 (shown as rectangles in FIG. 14B, even though they may be rectilinear cubes). These bounding boxes 1475, 1476, and 1477 are used to align the 3D models of prosthetic teeth 1470, 1471, and 1472 over the area to be reconstructed on the patient (as represented as part of 3D model of the lower teeth 1420). In some embodiments, the bounding boxes 1475, 1476, and 1477 are scaled, translated and/or otherwise aligned such that the bounding boxes, together, fill the entire area to be reconstructed. After the 3D models of the teeth 1470, 1471, and 1472 have been placed approximately using bounding boxes 1475, 1476, and 1477, the gaps (or overlaps) between neighboring teeth models 1470, 1471, and 1472 can be corrected or approximately corrected by, e.g., scaling and/or translating each tooth (as described with respect to FIGS. 15A and 15B and elsewhere herein).

In other embodiments, after one or more manipulation command are received, only the affected tooth or teeth may be manipulated, thereby leaving unchanged the placement, scale, and rotation of one or more of the 3D models of teeth in the virtual multi-tooth prosthesis. For example, if the manipulator 1490 in FIG. 14B is manipulated, then this may only affect the scale of the 3D models of prosthetic teeth 1470 and 1471. 3D model of prosthetic tooth 1472 may remain unchanged in position, scale, and/or rotation. After the two 3D models of teeth 1470 and 1471 have been scaled, translated, rotated, etc., any gap or overlap between them may be reduced or eliminated in the manner described with respect to FIGS. 15A and 15B and elsewhere herein.

In some embodiments, an initial placement or alignment of the 3D models of prosthetic teeth 1470, 1471, and 1472 can be obtained from any appropriate means, such as by referencing an alignment stored in a dental prosthesis library.

In some embodiments, the techniques may use bounding volumes or bounding boxes, not only for initial alignment of the 3D models of prosthetic teeth, but also for attempting to ensure that 3D models of neighboring teeth do not intersect or overlap in terms of volume. As neighboring teeth are scaled, for example, the bounding box can be used as a first approximation to ensure that neighboring teeth do not intersect or overlap in terms of volume. Similarly, when one of the 3D models of prosthetic teeth is translated, the bounding boxes may be used as a first approximation in order to ensure that the 3D models of prosthetic teeth do not intersect or overlap in terms of volume. The bounding boxes may also be used for rotation or any other manipulation of one or more teeth in the virtual multi-tooth prosthesis.

FIGS. 15A and 15B depict two neighboring teeth 1570 and 1571 and their respective bounding boxes 1590 and 1591. As depicted in FIG. 15A, after a first relative placement of the 3D models of the prosthetic teeth has been computed, a gap may exist between the neighboring teeth. In some embodiments, the gap is closed in order to increase the aesthetic appeal and/or function of the virtual multi-tooth prosthesis. In some embodiments, the smallest distance between the two models may be determined and the gap, as illustrated by 1595 and 1596, between the two models 1570 and 1571 may be determined. The models 1570 and 1571 may then be scaled and/or translated to close the gap represented by 1595 and 1596. In order to close the gap between the two 3D models 1570 and 1571, in some embodiments, each model may be scaled in the direction of the other model. In various embodiments, in order to close the gap between 3D models 1570 and 1571, the models may be scaled so that each 3D model 1570 and 1571 covers half of the distance (e.g., distance 1595 summed with distance 1596). The two 3D models 1570 and 1571, after scaling, are depicted in FIG. 15B. In FIG. 15B, the two models touch or nearly touch at point 1597.

In some embodiments, in order to close or approximately close a gap between neighboring teeth, each 3D model may be scaled to bring the closest points between the two 3D models 1570 and 1571 to the border of the two bounding boxes. For example, the model 1570 may be scaled by an amount to close the previous gap 1595 to bring the 3D model 1570 to the border of the two bounding boxes (and the same may be the case for model 1571). Other methods and techniques of closing the gaps between teeth are also possible and are considered within the scope of the embodiments herein. Further, in some embodiments, the gap between neighboring teeth may not be closed in a virtual multi-tooth prosthesis. Or a connector may be used to span the space between the neighboring teeth (not depicted in FIGS. 15A and 15B).

In the example of FIGS. 15A and 15B, the neighboring teeth have a gap (represented by distances 1595 and 1596). The techniques described herein can include removing or reducing an overlap of neighboring teeth (not shown in FIGS. 15A and 15B). For example, the neighboring teeth may be scaled (e.g., scaled to be smaller) and/or translated in order to remove the overlap between the neighboring teeth.

After modifying the virtual multi-tooth prosthesis based on the received manipulation commands in block 1330, then optionally, in block 1340, the virtual multi-tooth prosthesis may be modified based on occlusion with the antagonist. Modifying a prosthesis based on occlusion with antagonist teeth is described elsewhere herein. Once the virtual multi-tooth prosthesis has been modified, the prosthesis may be treated as a rigid object and occlusion of that rigid object may be calculated with respect to the antagonist and the entire virtual multi-tooth prosthesis may move as a single structure. In other embodiments, each individual 3D model of a tooth may be modified separately based on its own occlusion with the antagonist. These two techniques are described elsewhere herein.

As described above with respect to block 1330 and with respect to FIGS. 15A and 15B, if individual 3D models of teeth are modified in the virtual multi-tooth prosthesis based on occlusion with antagonist (block 1340), then gaps (or overlaps) may form between neighboring teeth. That is, after the occlusion is estimated and the individual 3D models of teeth have been moved with respect to one another, then a gap (or an overlap) may result between neighboring 3D models of teeth. Closing the gap (or avoiding the overlap) between neighboring teeth is described above. In the situation and embodiments in which the virtual multi-tooth prosthesis is moved as a rigid body, it is unlikely or impossible that an additional gap or overlap will be introduced between neighboring teeth and therefore there may be no gap or overlap to correct between neighboring teeth.

After performing block 1330 and/or block 1340, then, optionally, the virtual multi-tooth prosthesis may be presented relative to the area to be reconstructed in block 1310. Additionally, when the operator is ready to continue designing the multi-tooth prosthesis, the operator may continue to other steps not depicted in method 1300. Additionally, when the operator is ready to produce the multi-tooth prosthesis, the manufacturing data may be produced as part of block 1350.

FIG. 13B depicts another method 1301 for prosthesis manipulation in dental prosthesis design. In some embodiments, if a command is received to translate, scale, rotate, or otherwise manipulate an individual prosthetic tooth in the virtual prosthesis (block 1321), then the 3D model for that prosthetic tooth may be manipulated based on that command and occlusion may be estimated for either that individual tooth or for the virtual prosthesis as a whole (block 1331). For example, turning to FIG. 12, each time a 3D model of a prosthetic tooth 1270, 1271, and/or 1272 are translated, scaled, rotated, etc, the occlusion of that tooth with the antagonists may also be determined and the 3D model of the prosthetic tooth may be manipulated (e.g., moved based on motion simulation) with respect to the other 3D models of teeth.

Returning again to FIG. 13, in block 1311, a 3D model of a virtual prosthesis, possibly containing individual 3D models of individual prosthetic teeth, is presented relative to the area to be reconstructed. This is described generally with respect to block 1310. In block 1321, manipulation commands are received which are related to all or a portion of the prosthesis. The types of commands that may be received are described with respect to block 1320.

In block 1331, the prosthesis is modified based on the manipulation commands and based on the occlusion with antagonist teeth. Manipulation of the teeth is described above with respect to block 1330 and modifying the prosthesis based on occlusion with antagonist teeth is described above with respect to block 1340. After the prosthesis has been modified, both based on the manipulation command and based on the occlusion with antagonist teeth, the prosthesis may be again displayed relative to the area to be reconstructed in block 1311. Additionally, once the operator is happy with the virtual prosthesis or is ready to produce the prosthesis, the operator may continue to other steps in prosthesis design (not pictured) or may produce manufacturing data for the prosthesis (block 1350).

Other methods and techniques may be used. Further, other blocks may be added to each of methods 1300 and 1301, or the blocks may be executed in a different order, may be executed simultaneously, or may be left out altogether. Blocks from method 300, 301, 1300, and/or 1301 may be used together in any order and in any combination. For example, in some embodiments, the 3D model of the prosthetic tooth represents the outer surface of the prosthetic tooth. The inner portion of the 3D model of the prosthetic tooth may be associated with an implant, a prepared tooth, a gum surface, etc.—and may have an inner 3D surface designed to mate with the implant, prepared tooth, gum surface, etc. In some embodiments, if the 3D model of a prosthetic tooth is manipulated (block 1330 or block 1331) and/or modified based on occlusion (block 1340 or block 1331), then only the outer surface is manipulated or modified and the inner surface (which is mated with an implant, prepared tooth, gum surface, etc) may not be modified. As such, in various embodiments, manipulating or modifying the exterior surface of a tooth may not change how the tooth is mated with an underlying surface.

The processes and systems described herein may be performed on or encompass various types of hardware, such as computing devices. In some embodiments, computer 210, display 220, and/or input device 230 may each be separate computing devices, applications, or processes or may run as part of the same computing devices, applications, or processes—or one or more may be combined to run as part of one application or process—and/or each or one or more may be part of or run on computing devices. Computing devices may include a bus or other communication mechanism for communicating information, and a processor coupled with the bus for processing information. The computing devices may have a main memory, such as a random access memory or other dynamic storage device, coupled to the bus. The main memory may be used to store instructions and temporary variables. The computing devices may also include a read-only memory or other static storage device coupled to the bus for storing static information and instructions. The computer systems may also be coupled to a display, such as a CRT or LCD monitor. Input devices may also be coupled to the computing devices. These input devices may include a mouse, a trackball, or cursor direction keys.

Each computing device may be implemented using one or more physical computers, processors, embedded devices, or computer systems or a combination or portions thereof. The instructions executed by the computing device may also be read in from a computer-readable storage medium. The computer-readable storage medium may be a CD, DVD, optical or magnetic disk, laserdisc, carrier wave, or any other medium that is readable by the computing device. In some embodiments, hardwired circuitry may be used in place of or in combination with software instructions executed by the processor. Communication among modules, systems, devices, and elements may be over direct or switched connections, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering, including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements, and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable storage medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A computer-implemented method for occlusion estimation in dental prosthesis design, comprising:
   determining, using one or more computer processors, based on an initial relative placement of a first 3D computer model of teeth and a second 3D computer model of teeth, a first contact point on the first 3D computer model of teeth that is closest to the second 3D computer model of teeth, wherein the first 3D computer model of teeth and the second 3D computer model of teeth represent occluding teeth;

iteratively performing motion simulation of relative motion between the first 3D computer model of teeth and the second 3D computer model of teeth to estimate occlusion between the first 3D computer model of teeth and the second 3D computer model of teeth, said performing motion simulation comprising:

determining, using a first set of contact points between the first 3D model of teeth and the second 3D model of teeth, a second set of contact points, said first set of contact points initially comprising the first contact point;

determining a set of candidate contact points to use in a subsequent motion simulation iteration based on the second set of contact points; and determining whether the set of candidate contact points meets one or more predetermined stopping criteria and, if the set of candidate contact points do not meet one or more predetermined stopping criteria set, continuing iteratively performing motion simulation of relative motion between the first 3D computer model of teeth and the second 3D computer model of teeth to estimate occlusion between the first 3D computer model of teeth and the second 3D computer model of teeth; and when a particular set of candidate contact points meets the one or more predetermined stopping criteria, determining a new relative placement of the first 3D model of teeth and the second 3D model of teeth based at least in part on the particular set of candidate contact points and, upon determining the new relative placement of the first 3D computer model of teeth and the second 3D computer model of teeth, ending iteration.

2. The method of claim 1, wherein the method further comprises determining the second 3D computer model of teeth based at least in part on a scanned checkbite.

3. The method of claim 1, wherein the method further comprises determining the initial relative placement of the first 3D computer model of teeth with respect to the second 3D computer model of teeth at least in part based on a scanned checkbite.

4. The method of claim 1, wherein the method further comprises:

performing a scanning procedure to obtain the first 3D computer model of teeth and the second 3D computer model of teeth; and determining the initial relative placement of the first 3D computer model of teeth with respect to the second 3D computer model of teeth at least in part based on a relative placement during the performance of the scanning procedure.

5. The method of claim 1, wherein determining the first contact point comprises simulating gravity acting on the second 3D computer model of teeth.

6. The method of claim 1, wherein using simulated motion comprises using a rigid-body motion simulation.

7. The method of claim 1, wherein using simulated motion comprises using a six-degree-of-freedom motion simulation.

8. The method of claim 1, wherein the method further comprises determining the direction of gravity based on an occlusal plane of the first 3D computer model of teeth.

9. The method of claim 8, wherein the method further comprises determining the occlusal plane of the first 3D computer model of teeth by simulating movement of one of a planar object falling and the first 3D computer model of teeth with respect to the other.

10. The method of claim 1, wherein determining the second set of contact points comprises simulating the motion of the second 3D computer model of teeth with respect to the first 3D computer model of teeth until one or more contact points are determined.

11. The method of claim 1, wherein the method further comprises determining a center of gravity of the second 3D computer model.

12. The method of claim 1, wherein determining whether the set of candidate contact points meets one or more predetermined stopping criteria comprises determining whether there are two contact points in the set of candidate contact points that are on opposite sides of a center of gravity of the second 3D computer model.

13. The method of claim 1, wherein determining whether the set of candidate contact points meets one or more predetermined stopping criteria comprises determining whether there are three contact points in the set of candidate contact points that form a triangle encompassing a center of gravity of the second 3D computer model.

14. A system for occlusion estimation in dental prosthesis design, comprising one or more computing devices, said computing devices being configured to:

determine, based on an initial relative placement of a first 3D computer model of teeth and a second 3D computer model of teeth, a first contact point on the first 3D computer model of teeth that is closest to the second 3D computer model of teeth, wherein the first 3D computer model of teeth and the second 3D computer model of teeth represent occluding teeth;

iteratively perform motion simulation of relative motion between the first 3D computer model of teeth and the second 3D computer model of teeth to estimate occlusion between the first 3D computer model of teeth and the second 3D computer model of teeth, said performing motion simulation comprising:

determining, using a first set of contact points between the first 3D computer model of teeth and the second 3D computer model of teeth, a second set of contact points, said first set of contact points initially comprising the first contact point;

determining a set of candidate contact points to use in a subsequent motion simulation iteration based on the second set of contact points; and determining whether the set of candidate contact points meets one or more predetermined stopping criteria and, if the set of candidate contact points do not meet one or more predetermined stopping criteria set, continuing iteratively performing motion simulation of relative motion between the first 3D computer model of teeth and the second 3D computer model of teeth to estimate occlusion between the first 3D computer model of teeth and the second 3D computer model of teeth; and when a particular set of candidate contact points meets the one or more predetermined stopping criteria, determine a new relative placement of the first 3D computer model of teeth and the second 3D computer model of teeth based at least in part on the particular set of candidate contact points and, upon determining the new relative placement of the first 3D computer model of teeth and the second 3D computer model of teeth, ending iteration.

15. A non-transitory computer readable storage medium comprising computer-executable instructions for occlusion estimation in dental prosthesis design, said instructions embodied on the computer-readable storage medium in a non-transitory manner, said computer-executable instructions, when running on one or more computing devices, performing a method comprising:
- determining, using one or more computer processors, based on an initial relative placement of a first 3D computer model of teeth and a second 3D computer model of teeth, a first contact point on the first 3D computer model of teeth that is closest to the second 3D computer model of teeth, wherein the first 3D computer model of teeth and the second 3D computer model of teeth represent occluding teeth;
- iteratively performing motion simulation of relative motion between the first 3D model of teeth and the second 3D computer model of teeth, said performing motion simulation comprising:
  - determining, using a first set of contact points between the first 3D computer model of teeth and the second 3D computer model of teeth, a second set of contact points, said first set of contact points initially comprising the first contact point;
  - determining a set of candidate contact points to use in a subsequent motion simulation iteration based on the second set of contact points; and
  - determining whether the set of candidate contact points meets one or more predetermined stopping criteria and, if the set of candidate contact points do not meet one or more predetermined stopping criteria set, continuing iteratively performing motion simulation of relative motion between the first 3D computer model of teeth and the second 3D computer model of teeth to estimate occlusion between the first 3D computer model of teeth and the second 3D computer model of teeth; and
- when a particular set of candidate contact points meets the one or more predetermined stopping criteria, determining a new relative placement of the first 3D model of teeth and the second 3D model of teeth based at least in part on the particular set of candidate contact points and, upon determining the new relative placement of the first 3D computer model of teeth and the second 3D computer model of teeth, ending iteration.

16. The method of claim 1, further comprising performing a scanning procedure to obtain the first 3D computer model of teeth and the second 3D computer model of teeth.

17. The method of claim 1, further comprising receiving information from a scanning procedure to obtain the first 3D computer model of teeth and the second 3D computer model of teeth.

18. The method of claim 1, wherein determining whether the set of candidate contact points meets one or more predetermined stopping criteria comprises determining whether force normals on the first 3D computer model of teeth and the second 3D computer model of teeth are such that no additional rotation is possible in the motion simulation.

19. The method of claim 1, wherein the set of candidate contact points comprises at least one contact point from the second set of contact points.

20. The system of claim 14, wherein determining whether the set of candidate contact points meets one or more predetermined stopping criteria comprises determining whether there are two contact points in the set of candidate contact points that are on opposite sides of a center of gravity of the second 3D computer model.

21. The system of claim 14, wherein determining whether the set of candidate contact points meets one or more predetermined stopping criteria comprises determining whether there are three contact points in the set of candidate contact points that form a triangle encompassing a center of gravity of the second 3D computer model.

22. The method of claim 14, wherein determining whether the set of candidate contact points meets one or more predetermined stopping criteria comprises determining whether force normals on the first 3D model of teeth and the second 3D computer model of teeth are such that no additional rotation is possible in the motion simulation.

23. The system of claim 14, wherein the set of candidate contact points comprises at least one contact point from the second set of contact points.

24. The non-transitory computer readable storage medium of claim 15, wherein determining whether the set of candidate contact points meets one or more predetermined stopping criteria comprises determining whether there are two contact points in the set of candidate contact points that are on opposite sides of a center of gravity of the second 3D computer model.

25. The non-transitory computer readable storage medium of claim 15, wherein determining whether the set of candidate contact points meets one or more predetermined stopping criteria comprises determining whether there are three contact points in the set of candidate contact points that form a triangle encompassing a center of gravity of the second 3D computer model.

26. The non-transitory computer readable storage medium of claim 15, wherein determining whether the set of candidate contact points meets one or more predetermined stopping criteria comprises determining whether force normals on the first 3D computer model of teeth and the second 3D computer model of teeth are such that no additional rotation is possible in the motion simulation.

27. The non-transitory computer readable storage medium of claim 15, wherein the set of candidate contact points comprises at least one contact point from the second set of contact points.

* * * * *